US010787491B2

(12) United States Patent
Hinner et al.

(10) Patent No.: US 10,787,491 B2
(45) Date of Patent: Sep. 29, 2020

(54) NUCLEIC ACID MOLECULES ENCODING MUTEINS OF HUMAN LIPOCALIN 2 WITH AFFINITY FOR GLYPICAN-3 (GPC3)

(71) Applicant: Pieris Pharmaceuticals GmbH, Freising (DE)

(72) Inventors: Marlon Hinner, Munich (DE); Andrea Allersdorfer, Wolnzach (DE); Rachida Siham Bel Aiba, Munich (DE); Michaela Aloe, Freising (DE); Alexander Wiedenmann, Ulm (DE); Gabriele Matschiner, Munich (DE); Martin Huelsmeyer, Wolfersdorf (DE)

(73) Assignee: Pieris Pharmaceuticals GmbH, Hallbergmoos (DE)

( * ) Notice: Subject to any disclaimer, the term of this patent is extended or adjusted under 35 U.S.C. 154(b) by 0 days.

(21) Appl. No.: 16/389,115

(22) Filed: Apr. 19, 2019

(65) Prior Publication Data

US 2019/0309037 A1    Oct. 10, 2019

Related U.S. Application Data

(62) Division of application No. 15/575,271, filed as application No. PCT/EP2016/061058 on May 18, 2016, now Pat. No. 10,273,275.

(30) Foreign Application Priority Data

May 18, 2015  (EP) .................... 15167922

(51) Int. Cl.
| C07K 14/47 | (2006.01) |
| C12N 15/10 | (2006.01) |
| A61K 38/02 | (2006.01) |
| G01N 33/50 | (2006.01) |
| A61K 38/00 | (2006.01) |

(52) U.S. Cl.
CPC .......... *C07K 14/4725* (2013.01); *A61K 38/00* (2013.01); *A61K 38/02* (2013.01); *G01N 33/50* (2013.01); *C12N 15/102* (2013.01)

(58) Field of Classification Search
CPC .... C07K 14/4725; A61K 38/00; A61K 38/02; G01N 33/50; C12N 15/102
See application file for complete search history.

(56) References Cited

U.S. PATENT DOCUMENTS

| 5,728,553 A | 3/1998 | Goodey et al. |
| 5,849,576 A | 12/1998 | Skerra et al. |
| 6,099,517 A | 8/2000 | Daugherty |
| 6,103,493 A | 8/2000 | Skerra et al. |
| 6,123,936 A | 9/2000 | Platz et al. |
| 6,177,074 B1 | 1/2001 | Glue et al. |
| 6,403,564 B1 | 6/2002 | Ganguly et al. |
| 6,500,930 B2 | 12/2002 | Adamson |
| 6,620,413 B1 | 9/2003 | De Sauvage et al. |
| 6,696,245 B2 | 2/2004 | Winter et al. |
| 7,235,520 B2 | 6/2007 | Green et al. |
| 7,250,297 B1 | 7/2007 | Beste et al. |
| 7,252,998 B2 | 8/2007 | Skerra et al. |
| 7,585,940 B2 | 9/2009 | Skerra et al. |
| 8,313,924 B2 | 11/2012 | Jensen et al. |
| 8,986,951 B2 | 3/2015 | Hohlbaum et al. |
| 9,051,382 B2 | 6/2015 | Trentmann et al. |
| 9,260,492 B2 | 2/2016 | Matschiner et al. |
| 9,522,940 B2 | 12/2016 | Kirchfield |
| 9,549,968 B2 | 1/2017 | Skerra et al. |
| 9,884,898 B2 | 2/2018 | Corvey et al. |
| 10,273,275 B2 | 4/2019 | Hinner et al. |
| 2003/0069395 A1 | 4/2003 | Sato et al. |
| 2006/0058510 A1 | 3/2006 | Skerra et al. |
| 2006/0088908 A1 | 4/2006 | Skerra et al. |
| 2013/0079286 A1 | 3/2013 | Skerra et al. |
| 2013/0225505 A1 | 8/2013 | Robinson |
| 2013/0296258 A1 | 11/2013 | Matschiner et al. |
| 2015/0284435 A1 | 10/2015 | Kirchfield |
| 2017/0066807 A1 | 3/2017 | Olwill et al. |
| 2017/0114109 A1 | 4/2017 | Skerra et al. |
| 2017/0369542 A1 | 12/2017 | Trentmann et al. |
| 2018/0016312 A1 | 1/2018 | Bel Aiba et al. |

(Continued)

FOREIGN PATENT DOCUMENTS

| DE | 4417598 A1 | 12/1995 |
| DE | 19641876 A1 | 4/1998 |
| DE | 19742706 A1 | 4/1999 |

(Continued)

OTHER PUBLICATIONS

"Chain A Crystal Structure of Siderocalin (Ngal, Lipocalin 2) Complexed With Trencam-3,2-Hopo, A Cepabactin Analogue," GenBank Accession No. 1X71_A, Sep. 24, 2008.
Aina et al., From Combinatorial Chemistry to Cancer-Targeting Peptides, Molecular Pharmaceutics, Oct. 1, 2007, 4(5):631-651.
Altschul et al., Gapped BLAST and PSI-BLAST: a new generation of protein database search programs, Nucleic Acids Res., 25(17):3389-3402 (1997).
Altschul, S. et al., Basic Local Alignment Search Tool; J. Mol. Biol., 215:403-410 (1990).
Altuvia et al., Ranking potential binding peptides to MHC molecules by a computational threading approach, J. Mol. Biol., 1995, 249:244-250.
Amstutz, P. et al., In vitro display technologies: novel developments and applications, Curr. Opin. Biotechnol., 2001, 12:400-405.

(Continued)

*Primary Examiner* — Robert S Landsman
(74) *Attorney, Agent, or Firm* — Choate, Hall & Stewart, LLP; Brian E. Reese; Dana M. Daukss

(57) ABSTRACT

The present disclosure relates to novel, specific-binding therapeutic and/or diagnostic proteins directed against Glypican-3 (GPC3), which proteins preferably are muteins of a lipocalin protein, more preferably of lipocalin 2 (Lcn2 or NGAL). Present disclosure also relates to nucleic acid molecules encoding such proteins and to methods for generation and use of such proteins and nucleic acid molecules. Accordingly, present disclosure also is directed to pharmaceutical and/or diagnostic compositions comprising such lipocalin proteins, including uses of these proteins.

11 Claims, 1 Drawing Sheet

Specification includes a Sequence Listing.

(56) References Cited

U.S. PATENT DOCUMENTS

| | | |
|---|---|---|
| 2018/0141988 A1 | 5/2018 | Hinner et al. |
| 2018/0148484 A1 | 5/2018 | Hinner et al. |

FOREIGN PATENT DOCUMENTS

| | | |
|---|---|---|
| DE | 19926068 C1 | 1/2001 |
| EP | 0 330 451 A2 | 8/1989 |
| EP | 0 361 991 A2 | 4/1990 |
| JP | 2005503829 A | 2/2005 |
| JP | 2007284351 A | 11/2007 |
| WO | WO-96/23879 A1 | 8/1996 |
| WO | WO-98/16873 A1 | 4/1998 |
| WO | WO-99/16873 A1 | 4/1999 |
| WO | WO-99/064016 A1 | 12/1999 |
| WO | WO-00/075308 A1 | 12/2000 |
| WO | WO-03/029462 A1 | 4/2003 |
| WO | WO-03/029463 A2 | 4/2003 |
| WO | WO-03/029471 A1 | 4/2003 |
| WO | WO-2005/019254 A1 | 3/2005 |
| WO | WO-2005/019255 A1 | 3/2005 |
| WO | WO-2005/019256 A2 | 3/2005 |
| WO | WO-2006/056464 A2 | 6/2006 |
| WO | WO-2007/038619 A2 | 4/2007 |
| WO | WO-2007/047291 A2 | 4/2007 |
| WO | WO-2007/137170 A2 | 11/2007 |
| WO | WO-2008/015239 A2 | 2/2008 |
| WO | WO-2009/012394 A1 | 1/2009 |
| WO | WO-2009/052390 A1 | 4/2009 |
| WO | WO-2009/156456 A1 | 12/2009 |
| WO | WO-2011/069992 A2 | 6/2011 |
| WO | WO-2011/149962 A1 | 12/2011 |
| WO | WO-2011/154420 A2 | 12/2011 |
| WO | WO-2012/065978 A1 | 5/2012 |
| WO | WO-2013/174783 A1 | 11/2013 |

OTHER PUBLICATIONS

Bachmann, Barbara J., Linkage Map of *Escherichia coli* K-12. Edition 8, Microbial. Rev., Jun. 1990, 54(2):130-197.

Beck, et al., Nucleotide Sequence and Genome Organisation of Filamentous Bacteriophages f1 and fd, Gene, vol. 16, pp. 35-58, 1981.

Beste, G. et al., Small antibody-like proteins with prescribed ligand specificities derived from the lipocalin fold, Proc. Natl. Acad. Sci. USA, Mar. 1999, 96:1898-1903.

Binder et al., High-throughput sorting of an anticalin library via EspP-mediated functional display on the *Escherichia coli* cell surface, Journal of Molecular Biology, Jul. 23, 2010, 400(4):783-802.

Bittker, J. et al., Nucleic acid evolution and minimization by nonhomologous random recombination, Nat. Biotechnol., Oct. 2002, 20:1024-1029.

Bork, Peer, Powers and Pitfalls in Sequence Analysis: The 70% Hurdle, Genome Research, 2000, vol. 10, pp. 398-400.

Bos et al., OctoDEX.TM.—Controlled Release of Pharmaceutical Proteins from Hydrogels, Business Briefing: Pharmatech, 2003:1-6.

Breustedt, D. et al., Comparative ligand-binding analysis of ten human lipocalins, Biochim. Biophys. Acta, 2006, 1764:161-173.

Broders, O et al., Hyperphage. Improving antibody presentation in phage display, Methods Mol. Biol., 2003, 205:295-302.

Brody et al., Active and Passive Immunotherapy for Neurodegenerative Disorders, Annu. Rev. Neurosci., 2008, 31:175-193.

Bruckdorfer, T., et al., From Production of Peptides in Milligram Amounts for Research to Multi-Tons Quantities for Drugs of the Future, Curr. Pharm. Biotechnol., 2004, 5:29-43.

Bullock, W. et al., XL1-Blue: A High Efficiency Plasmid Transforming recA *Escherichia coli* Strain with Beta-Galactosidase Selection, Biotechniques, 1987, 5(4):376-378.

Bundgaard, J.R. et al., Molecular Cloning and Expression of A cDNA Encode NGAL: A Lipocalin Expressed in Human Neutrophils, Biochemical and Biophysical Research Communications, Aug. 15, 1994, pp. 1468-1475, vol. 202, No. 3, XP002036694.

Carnemolla et al., Phage Antibodies with PAN-Species Recognition of the Oncofoetal Angiogenesis Marker Fibronectin ED-B Domain, Int. J. Cancer, 1996, 68:397-405.

Chan et al., The primary structure of rat α 2μ globulin-related protein, Nucleic Acids Research, vol. 16, No. 23, pp. 11368, 1988.

Coles, et al., The Solution Structure and Dynamics of Human Neutrophil Gelatinase-associated Lipocalin, J. Mol. Biol., vol. 289, pp. 139-157, 1999.

Dennis, M. et al., Albumin Binding as a General Strategy for Improving the Pharmacokinetics of Proteins, J. Biol. Chem., Sep. 20, 2002, 277(38):35035-35043.

Dodel et al., Immunotherapy for Alzheimer's disease, Lancet Neurology, Apr. 2003, 2:215-220.

Doerks et al., Protein annotation: detective work for function prediction, Trends in Genetics, 1998, vol. 14, pp. 248-250.

Ebbinghaus et al., Diagnostic and Therapeutic Applications of Recombinant Antibodies: Targeting the Extra-Domain B of Fibronectin, A Marker of Tumor Angiogenesis, Curr. Pharm. Des., 2004, 10:1537-1549.

Fitzgerald, Kevin, In Vitro Display Technologies—New Tools for Drug Discovery, Reviews, vol. 5, No. 6, pp. 253-258, Jun. 2000.

Fling, S. and Gregerson, D., Peptide and Protein Molecular Weight Determination by Electrophoresis Using a High-Molarity Tris Buffer System without Urea, Anal. Biochem., 1986, 155:83-88.

Flower et al., The lipocalin protein family: structural and sequence overview, Biochimica et Biophysica Acta, 2000, 1482:9-24.

Flower, Darren R., The lipocalin protein family: structure and function, Biochem. J., 1996, 318:1-14.

Frank, Ronald, The SPOT-synthesis technique Synthetic Peptide arrays on membrane supports—principles and applications, J. Immunol. Methods, 2002, 267:13-26.

Fuerteges, F. and Abuchowski, A., The Clinical Efficacy of Poly(Ethylene Glycol)-Modified Proteins,: J. Control. Release, 1990, 11:139-148.

Fujii, Phage display and beyond antibody—molecular target by antibody molecule, Seikagaku, 2010, vol. 82, No. 8, pp. 710-726, Abstract.

Gaillard, P. et al., Diphtheria toxin receptor-targeted brain drug delivery, International Congress Series., 2005, 1277:185-198.

Gaillard, P. et al., Targeted delivery across the blood-brain barrier, Expert Opin Drug Deliv., 2005, 2(2):299-309.

Gasteiger et al., ExPASy: the proteomics server for in-depth protein knowledge and analysis, Nucleic Acids Res., 2003, 31(13):3784-3788.

Gebauer et al., Engineered protein scaffolds as next-generation antibody therapeutics, Current Opinion in Chemical Biology, Jun. 1, 2009, 13:245-255.

Goetz, D. et al., Ligand Preference Inferred from the Structure of Neutrophil Gelatinase Associated Lipocalin, Biochemistry, 2000, 39:1935-1941.

Gronwall et al., Selection and characterization of Affibody ligands binding to Alzheimer amyloid β peptides, J. Biotechnol., 2007, 128:162-183.

Haass et al., Soluble protein oligomers in neurodegeneration: lessons from the Alzheimer's amyloid β-peptide, Nat. Rev. Mol. Cell. Biol., Feb. 2007, 8:101-112.

Hengen, Paul N., Methods and Reagents, Trends Biochem. Sci., vol. 21, pp. 75-76, 1996.

Ho et al Glypican-3: A new target for cancer immunotherapy, European Journal of Cancer, Feb. 2011, 47(3):333-338.

Hoess, Ronald H., Phage Display of Peptides and Protein Domains, Structural Biology, vol. 3, pp. 572-279, 1993.

Holhbaum, et al., Anticalins (R): The lipocalin family as a novel protein scaffold for the development of next-generation immunotherapies, Expert Review of Clinical Immunology, Jan. 1, 2007, 3(4):491-501.

Holliger et al., Diabodies small bivalent and bispecific antibody fragments, PNAS, Jul. 1993, 90:6444-6448.

(56) References Cited

OTHER PUBLICATIONS

Holzfeind, P. et al., Structural Organization of the Gene Encoding the Human Lipocalin Tear Prealbumin and Synthesis of the Recombinant Protein in *Escherichia coli*, Gene, vol. 139, pp. 177-183, 1994.

Hortschansky et al., The aggregation Kinetics of Alzheimer's β-amyloid peptide is controlled by stochastic nucleation, Protein Sci., 2005, 14:1753-1759.

Hoyer, W. et al., Stabilization of a β-hairpin in monomeric Alzheimer's amyloid-β peptide inhibits amyloid formation, Proc. Natl. Acad. Sci. USA, Apr. 1, 2008, 105(13):5099-5104.

Ill et al., "Design and construction of a hybrid immunoglobulin domain with properties of both heavy and light chain variable regions," Protein Engineering, 1997, 10(8):949-957.

International Search Report and Written Opinion issued in corresponding application No. PCT/EP2016/061058 dated Sep. 28, 2016.

International Search Report and Written Opinion of the International Searching Authority issued in International Application No. PCT/EP2011/070119 dated Jun. 3, 2012.

Jakubovic, B. and Jothy, S., Glypican-3: From the mutations of Simpson-Golabi-Behmel genetic syndrome to a tumor marker for hepatocellular carcinoma, Experimental and Molecular Pathology, 82:184-189 (2007).

Karlsson et al., Kinetic analysis of monoclonal antibody-antigen interactions with a new biosensor based analytical system, J. Immunol. Methods, 1991, 145:229-240.

Kaspar et al., Fibronectin as target for tumor therapy, Int. J. Cancer, 2006, 118:1331-1339.

Kaufman et al., Transgenic Analysis of 100-kb Human beta-Globin Cluster-Containing DNA Fragment Propagated as a Bacterial Artificial Chromosome, Blood, 1999, 94:3178-3184.

Kay et al., High-throughput screening strategies to identify inhibitors of protein-protein interactions, Molecular Diversity, 1995, 1:139-140.

Khurana et al., Mechanism of thioflavin T binding to amyloid fibrils, J. Struct. Biol., 2005, 151:229-238.

Kim, H. et al., High-Affinity Recognition of Lanthanide(III) Chelate Complexes by a Reprogrammed Human Lipocalin 2, J. Am. Chem. Soc., 2009, 131:3565-3576.

Kjelsden, L. et al., Human Neutrophil Gelatinase-Associated Lipocalin and Homologous Proteins in Rat and Mouse, Biochimica et Biophysica Acta, vol. 1482, pp. 272-283, 2000.

Konig, T. and Skerra, A., Use of an albumin-binding domain for the selective immobilization of recombinant capture antibody fragments on ELISA plates, J. Immunol. Methods, 1998, 218:73-83.

Korean Office Action issued in corresponding application No. 10-2012-7017730 dated Jul. 28, 2018 with English translation.

Kraulis, et al., The Serum Albumin-Binding Domain of Streptococcal Protein G is a Three-Helical Bundle: A Heteronuclear NMR Study, FEBS Letters, vol. 378, pp. 190-194, 1996.

Leahy et al., Crystallization of a Fragment of Human Fibronectin: Introduction of Methionine by Site-Directed Mutagenesis to Allow Phasing via Selenomethionine, Proteins, 1994, 19:48-54.

Lee et al., Targeting of hepatocellular carcinoma with glypican-3-targeting peptide ligand, Journal of Peptide Science, published online Oct. 4, 2011, 17(11):763-769.

Lichtlen et al., Antibody-based approaches in Alzheimer's research: safety, pharmacokinetics, metabolism, and analytical tools, J. Neurochem., 2007, 104:859-874.

Lohrengel, B. et al., Expression and Purification of Woodchuck Tumour Necrosis Factor Alpha, Cytokine, vol. 12, No. 6, pp. 573-577, Jun. 2000.

Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.

Lowman, H.B. Bacteriophage display and discovery of peptides leads for drug development, Annu. Rev. Biophys. Biomol. Struct., 1997, 26:401-424.

Martin et al., The affinity-selection of a minibody polypeptide inhibitor of human interleukin-6, The EMBO Journal, 1994, 13(22):5303-5309.

Mateo, C. et al., Removal of Amphipathic Epitopes from Genetically Engineered Antibodies: Production of Modified Immunoglobulins with Reduced Immunogenicity, Hybridoma, 2000, 19(6):463-471.

Meidan et al., Emerging Technologies in Transdermal Therapeutics, Am. J. Ther., 2004, 11(4):312-316.

Moretto et al., Conformation-sensitive Antibodies against Alzheimer Amyloid-β by Immunization with a Thioredoxin-constrained B-cell Epitope Peptide, J. Biol. Chem., 2007, 282(15):11436-11445.

Murakami, H. et al., Random insertion and deletion of arbitrary number of bases for codon-based random mutation of DNAs, Nat. Biotechnol., Jan. 2002, 20:76-81.

Nakatsura et al., Usefulness of the novel oncofetal antigen glypican-3 for diagnosis of heptocellular carcinoma and melanoma, BioDrugs, 2005, 19(2):71-77.

Notice of Reasons for Rejections dated Jan. 20, 2015 issued in Japanese Application No. 2012-542505, with English translation.

Osborn, B. et al., Pharmacokinetic and Pharmacodynamic Studies of a Human Serum Albumin-Interferon-α Fusion Protein in Cynomolgus Monkeys, J. Pharmacol. Exp. Ther., 2002, 303(2):540-548.

Paine et al., The Lipocalin website, Elsevier Science B.V., Biochimica et Biophysica Acta 1482, pp. 351-352, 2000.

Papiz, et al., The Structure of Beta-Lactoglobulin and Its Similarity to Plasma Retinol-Binding Protein, Nature, vol. 324, pp. 383-385, 1986.

Parikh et al., "Hepatocellular cancer: A guide for the internist," The American Journal of Medicine, 2007, 120:194-202.

Pervaiz, et al., Homology and Structure-Function Correlations Between α1-Acid Glycoprotein and Serum Retinol-Binding Protein and Its Relatives, 1987, The FASEB journal 1.3 (1987): 209-214.

Pini et al., Design and Use of a Phage Display Library, J. Biol. Chem., Aug. 21, 1998, 273(34):21769-21776.

Pini, A. et al., Phage Display and Colony Filter Screening for High-Throughput Selection of Antibody Libraries, Comb. Chem. High Throughput Screen., 2002, 5:503-510.

Pujuguet et al., Expression of Fibronectin ED-A+ and ED-B+ Isoforms by Human and Experimental Colorectal Cancer, Am. J. Pathol., Feb. 1996, 148(2):579-592.

Redl, Bernhard, Human tear lipocalin, Biochim. Biophys. Acta, 2000, 1482:241-248.

Roberts, Richard W., Totally In Vitro Protein Selection Using mRNA-Protein Fusions and Ribosome Display, Current Opinion in Chemical Biology, vol. 3, pp. 268-273, 1999.

Rodi, D. and Makowski, L., Phage-display technology—finding a needle in a vast molecular haystack, Curr. Opin. Biotechnol., 1999, 10:87-93.

Sasisekharan et al., Roles of heparan-sulphate glycosaminoglycans in cancer, Nature Reviews Cancer, Jul. 2002, 2:521-528.

Schiweck et al., Fermenter production of an artificial fab fragment rationally designed for the antigen cystatin and its optimized crystallization through constant domain shuffling, Proteins: Structure, Function, and Genetics, 1995, 23:561-565.

Schlehuber, S. and Skerra, A. et al., Duocalins, engineered ligand-binding proteins with dual specificity derived from the lipocalin fold, Biol. Chem., Sep. 2001, 382:1335-1342.

Schlehuber, S. and Skerra, A., Tuning ligand affinity, specificity, and folding stability of an engineered lipocalin variant—a so-called 'anticalin'—using a molecular random approach, Biophysical Chemistry 96 (2002) 213-228.

Schlehuber, S. et al., A Novel Type of Receptor Protein, Based on the Lipocalin Scaffold, with Specificity for Digoxigenin, J. Mol. Biol., 2000, 297:1105-1120.

Schliemann et al., Antibody-based targeting of the tumor vasculature, Biochim. Biophys. Acta, 2007, 1776:175-192.

Schmidt et al., The Strep-tag system for one-step purification and high-affinity detection of capturing of proteins, Nat. Protoc., 2007, 2(6):1528-1535.

Schmidt, T. et al., Molecular Interaction Between the Strep-tag Affinity Peptide and its Cognate Target, Streptavidin, J. Mol. Biol., 1996, 255:753-766.

(56) References Cited

OTHER PUBLICATIONS

Schoepfer, Ralf, The pRSET Family of T7 Promoter Expression Vectors for *Escherichia coli*, Gene, vol. 124, pp. 83-85, 1993.
Schonfeld, D. et al. An engineered lipocalin specific for CTLA-4 reveals a combining site with structural and conformational features similar to antibodies, PNAS, 106(20): 8198-8203 (2009).
Silverman et al., Multivalent avimer proteins evolved by exon shuffling of a family of human receptor domains, Nature Biotechnology, Dec. 2005, 23(12):1556-1561.
Skerra et al., 'Anticalins': a new class of engineered ligand-binding proteins with antibody-like properties, Reviews in Molecular Biotechnology, 2001, 74:257-275.
Skerra et al., Use of the Strep-tag and streptavidin for detection and purification of recombinant proteins, Methods in Enzymology, 2000, 326:271-304.
Skerra, A., et al., Lipocalins as a scaffold, Elsevier Science B.V., Biochimica et Biophysica Acta 1482, pp. 337-350, 2000.
Skerra, Anticalins as alternative binding proteins for therapeutic use; Current Opinion in Molecular Therapeutics, 9(4): 336-344 (Aug. 2007).
Skerra, Arne, Use of the tetracycline promoter for the tightly regulated production of a murine antibody fragment in *Escherichia coli*, Gene, 1994, 151:131-135.
Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.
Skolnick, J. et al., From genes to protein structure and function: novel applications of computational approaches in the genomic era, Trends in Biotech, 2000, vol. 18, No. 1, pp. 34-39.
Stoesz, S. et al., Overexpression of neu-related lipocalin (NRL) in neu-initiated but not ras or chemically initiated rat mammary carcinomas, Oncogene (1995), 11, pp. 2233-2241.
Studier, F.W., and Moffatt, B.A., Use of Bacteriophage T7 RNA Polymerase to Direct Selective High-level Expression of Cloned Genes, J. Mol. Biol., 1986, 189:113-130.
Tartof et al., Improved Media for Growing Plasmid and Cosmid Clones, Focus, Bethesda Research Laboratory, 1987, 9(2):12.
Tokuriki, N. and Tawflik, D., Stability effects of mutations and protein evolvability, Current Opinion in Structural Biology, 2009, vol. 19, pp. 596-604.
Traunecker et al., Bispecific single chain molecules (Janusins) target cytotoxic lymphocytes on HIV infected cells, The EMBO Journal, 1991, 10(12):3655-3659.
Traunecker et al., Janusin: New molecular design for bispecific reagents, International Journal of Cancer, 1992, 7:51-52.
Tulasne, D. et al., C-Terminal Peptide of Thrombospondin-1 Includes Platelet Aggregation Through the FC Receptor γ-Chain-Associated Signaling Pathway and by Agglutination, Blood, vol. 98, No. 12, pp. 3346-3352, Dec. 1, 2001.
Vajo, Z. and Duckworth, W., Genetically Engineered Insulin Analogs: Diabetes in the New Millennium, Pharmacol. Rev., 2000, 52(1):1-9.
Venturi, M. et al., High Level Production of Functional Antibody Fab Fragments in an Oxidizing Bacterial Cytoplasm, J. Mol. Biol., 2002, 315:1-8.
Virnekas et al., Trinucleotide phosphoramidites: ideal reagents for the synthesis of mixed oligonucleotides for random mutagenesis, Nucleic Acids Res, 1994, 22(25):5600-5607.
Vogt et al., "Bacterially produced apolipoprotein D binds progesterone and arachidonic acid, but not bilirubin or E-3M2H," Journal of Molecular Recognition, 2001, 14:79-86.
Vogt, M. and Skerra, A., Construction of an Artificial Receptor Protein ("Anticalin") Based on the Human Apolipoprotein D, ChemBioChem, 5: 191-199 (2004).
Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.
Wang et al., Expanding the Genetic Code of *Escherichia coli*, Science, Apr. 20, 2001, 292:498-500.
Wang et al., Expanding the genetic code, Chem. Comm., 2002, 1:1-11.
Wang et al., Rapid analysis of gene expression (RAGE) facilitates universal expression profiling, Nucleic Acids Research, 1999, 27(23):4609-4618.
Wang, A. M. et al., Molecular Cloning of the Complementary DNA for Human Tumor Necrosis Factor, Science, vol. 228, pp. 149-154, 1985 (Abstract).
Wawrzynczak, E.J., Systemic immunotoxin therapy of cancer: advances and prospects, Br. J. Cancer, 64:624-630 (1991).
Wells, J. et al., Rapid Evolution of Peptide and Protein Binding Properties In Vitro, Current Opinion in Structural Biology, vol. 2, pp. 597-604, 1992.
Wells, James A., Additivity of Mutational Effects in Proteins, Biochemistry, Sep. 18, 1990, 29(37):8509-8517.
Wilson, D. et al., The use of mRNA display to select high-affinity protein-binding peptides, Proc. Natl. Acad. Sci. USA, Mar. 27, 2001, 98(7):3750-3755.
Yanisch-Perron, C. et al., Improved M13 phage cloning vectors and host strains: nucleotide sequences of the M13mp18 and pUC19 vectors, Gene, 1985, 33:103-119.
Zaccolo, M.et al., An Approach to Random Mutagenesis of DNA Using Mixtures of Triphosphate Derivatives of Nucleoside Analogues, J. Mal. Biol., 1996, 255:589-603.
Zardi, L. et al., Transformed human cells produce a new fibronectin isoform by preferential alternative splicing of a previously unobserved exon, EMBO J, 6(8):2337-42 (1987).

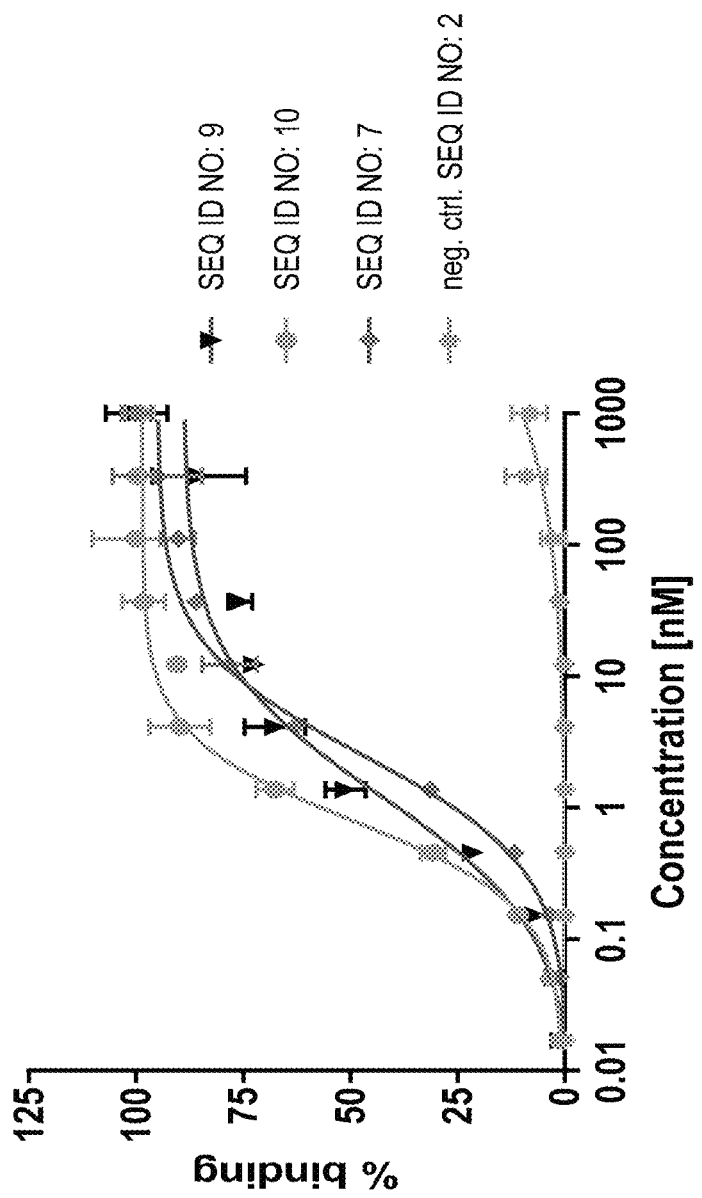

NUCLEIC ACID MOLECULES ENCODING MUTEINS OF HUMAN LIPOCALIN 2 WITH AFFINITY FOR GLYPICAN-3 (GPC3)

CROSS REFERENCE TO RELATED APPLICATIONS

The present application is a division of U.S. patent application Ser. No. 15/575,271, filed Nov. 17, 2017, now U.S. Pat. No. 10,273,275, which is a national stage entry of International Patent Application No. PCT/EP2016/061058, filed May 18, 2016, which claims priority to European Patent Application No. 15167922.2 filed May 18, 2015, each of which is incorporated herein by reference in its entirety.

I. BACKGROUND

Glypican-3 (GPC3) is an oncofetal antigen that belongs to the glypican family of glycosyl-phosphatidylinositol-anchored heparin sulfate proteoglycans. Glypicans are characterized by a covalent linkage to complex polysaccharide chains called heparinsulphate glycosaminoglycans. Glypicans are involved in cell signaling at the cellular-extracellular matrix interface. (Sasisekharan et al., Nat. Rev. Cancer 2:521-528 (2002).) To date, six distinct members of the human glypican family have been identified. Cell membrane-bound GPC3 is composed of two subunits, linked by one or more disulfide bonds.

GPC3 is expressed in fetal liver and placenta during development and is down-regulated or silenced in normal adult tissues. Mutations and depletions in the GPC3 gene are responsible for the Simpson-Golabi-Behmel or Simpson dysmorphia syndrome in humans. GPC3 is expressed in various cancers and, in particular, hepatocellular carcinoma ("HCC"), melanoma, Wilm's tumor, and hepatoblastoma. (Jakubovic and Jothy, Ex. Mol. Path. 82:184-189 (2007); Nakatsura and Nishimura, Biodrugs 19(2):71-77 (2005).)

HCC is the third leading cause of cancer-related deaths worldwide. Each year, HCC accounts for about 1 million deaths. (Nakatsura and Nishimura, Biodrugs 19(2):71-77 (2005).) Hepatitis B virus, hepatitis C virus, and chronic heavy alcohol use leading to cirrhosis of the liver remain the most common causes of HCC. The incidence of HCC has increased dramatically in the United States, in part because of the spread of the hepatitis C virus. HCC is treated primarily by liver transplantation or tumor resection. Patient prognosis is dependent on both the underlying liver function and the stage at which the tumor is diagnosed. (Parikh and Hyman, Am J Med. 120(3):194-202 (2007).) Effective strategies for the treatment of HCC and other tumors expressing GPC3 are needed. It would thus be desirable to have available means and methods for targeting GPC3, preferably GPC3 expressed on tumor cells.

International Patent Application No. PCT/EP2011/070119 disclosed lipocalin muteins, derived from human lipocalin 2 (also called human neutrophil gelatinase-associated lipocalin (hNGAL)), which are capable of binding GPC3. The present disclosure, however, provides additional GPC3-binding proteins having advanced features attendant to these proteins.

II. DESCRIPTIONS OF FIGURES

FIG. 1: shows binding of selected optimized GPC3 specific lipocalin muteins (SEQ ID NOs: 7, 9 and 10) on SK-HEP-1 cells transfected with human GPC3 as measured in an MSD-based assay. Optimized clones bind GPC3 positive cells with subnanomolar to low nanomolar EC50 values, while no significant binding of the negative control lipocalin (SEQ ID NO: 2) is detected. Similar binding is observed with SK-HEP-1 cells transfected with mouse or cynomolgus GPC3, whereas lipocalin muteins do not bind control cells (SK-HEP-1::vector).

III. DETAILED DESCRIPTION OF PRESENT DISCLOSURE

One embodiment of the current disclosure relates to a lipocalin mutein that is capable of binding human GPC3 with an affinity measured by a $K_D$ of about 1 nM or lower. More preferably, the mutein can have an affinity measured by a $K_D$ of about 1 nM or about 0.2 nM or lower. In another embodiment, the mutein is capable of competing for binding to human GPC3 in a cell-binding assay, such as an assay essentially described in Example 5, preferably with an EC50 value of about 25 nM, 10 nM or 3 nM or lower.

In another embodiment, the disclosure relates to a lipocalin mutein, wherein said mutein comprises at one or more positions corresponding to position 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of hNGAL (SEQ ID NO: 1) a substitution, preferably a substitution as described herein.

In particular embodiments, the mutein of the disclosure comprises at least 1, 2, 3, 4, 5, 6, 7, 8, 9, 10, 11, 12, 13, 14, 15, 16, 17, 18, 19 or 20, or even more such as 21, 22, 23, 24, 25 or 26, substitutions at a sequence position corresponding to sequence position 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of mature hNGAL (SEQ ID NO: 1).

In further particular embodiments, a lipocalin mutein according to the current disclosure comprises an amino acid sequence selected from the group consisting of SEQ ID NOs: 5-16. In another embodiment, the mutein has at least 70% identity to the sequence of mature hNGAL (SEQ ID NO: 1). Preferably, said mutein comprises 1, 2, 3, 4, 5, 6, 7, 8, 9, 10, 11, 12, 13, 14, 15, 16, 17, 18, 19 or 20, or even more such as 21, 22, 23, 24, 25 or 26, mutated amino acid residues at the sequence positions 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of mature hNGAL (SEQ ID NO: 1).

In some additional embodiments, in order to facilitate expression in eukaryotic cells, the natural N-glycosylation site Asn at position 65 of the linear polypeptide sequence of mature hNGAL (SEQ ID NO: 1) is removed at the corresponding sequence position of a lipocalin mutein according to the current disclosure, for example, by the mutation from Asn to Asp at position 65. Furthermore, it is preferred that N-glycosylation sites (Asn-X-Ser/Thr) do not exist on a lipocalin mutein according to the current disclosure.

In some other embodiments, a lipocalin mutein according to the current disclosure does not comprise a mutation at the sequence position corresponding to sequence position 28 of the linear polypeptide sequence of mature hNGAL (SEQ ID NO: 1), for example, in order to further optimize stability.

In another embodiment, the mutein of the current disclosure is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, and colloidal gold. The mutein can be fused at its N-terminus and/or its C-terminus to a fusion partner which is a protein, a protein domain, or a peptide.

In another embodiment, the mutein is conjugated to a compound that extends the serum half-life of the mutein. More preferably, the mutein is conjugated to a compound selected from the group consisting of a polyalkylene glycol molecule, a hydroethylstarch, an Fc part of an immunoglubolin, a CH3 domain of an immuoglubolin, a CH4 domain of an immunoglubolin, an albumin binding peptide, and an albumin binding protein.

In another embodiment, the mutein of the current disclosure is an antagonist of a GPC3.

In another embodiment, the current disclosure relates to a nucleic acid molecule comprising a nucleotide sequence encoding a mutein of the current invention.

In yet another embodiment, present disclosure encompasses a host cell containing said nucleic acid molecule.

The present disclosure also includes a method of treating a tumor, preferably liver tumor or melanoma, the method comprising administering a pharmaceutical composition containing a mutein as described herein to a subject in need thereof.

In one aspect, the present disclosure relates to novel, specific-binding proteins directed against or specific for GPC3. Proteins of the disclosure may be used for therapeutic and/or diagnostic purposes. A protein of the disclosure includes particularly an hNGAL mutein as described herein. As used herein, a protein of the disclosure "specifically binds" a target (here, GPC3) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

Likewise, in another aspect, the disclosure relates to an hNGAL mutein, wherein said mutein comprises at one or more positions corresponding to position 36, 40, 41, 49, 52, 68, 70, 72, 73, 77, 79, 81, 96, 100, 103, 106, 125, 127, 132, and/or 134 of the linear polypeptide sequence of mature hNGAL (SEQ ID NO: 1) a substitution, preferably a substitution as described herein.

In an alternative aspect, present disclosure relates to a polypeptide comprising an hNGAL mutein, wherein the hNGAL mutein comprises at 1, 2, 3, 4, 5, 6, 7, 8, 9, 10, 11, 12, 13, 14, 15, 16, 17, 18, 19, or 20 or even more, such as 21, 22, 23, 24, 25 or 26, amino acid positions corresponding to positions 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of mature hNGAL (SEQ ID NO: 1) a substitution, preferably a substitution as described herein.

Similarly, the disclosure relates to a lipocalin mutein derived from hNGAL having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind GPC3, non-natural target, with detectable affinity. Advantageously, the lipocalin mutein comprises at 1, 2, 3, 4, 5, 6, 7, 8, 9, 10, 11, 12, 13, 14, 15, 16, 17, 18, 19 or 20 amino acid position(s) corresponding to the amino acid at position 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of hNGAL (SEQ ID NO: 1) a substitution, preferably a substitution as described herein.

The present disclosure also relates to nucleic acids encoding these proteins.

The term "position" when used in accordance with present disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with present disclosure which may be substituted may very due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild type lipocalin 5'-untranslated region (UTR) including the promoter and/or any other regulatory sequences or gene (including exons and introns).

Thus, under a "corresponding position" in accordance with present disclosure it is preferably to be understood that nucleotides/amino acids may differ in the indicated number but may still have similar neighboring nucleotides/amino acids. Said nucleotides/amino acids which may be exchanged, deleted or added are also comprised by the term "corresponding position".

Specifically, in order to determine whether a nucleotide residue or amino acid residue of the amino acid sequence of a lipocalin different from an hNGAL lipocalin mutein of the disclosure corresponds to a certain position in the nucleotide sequence or the amino acid sequence of an hNGAL lipocalin mutein as described, in particular any of SEQ ID NOs: 5-16 or that having one or more amino acid substitutions at position 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of NGAL (SEQ ID NO: 1), a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a mutein of any of SEQ ID NOs: 1-8 or that having one or more amino acid substitutions at position 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of hNGAL (SEQ ID NO: 1) can serve as "subject sequence", while the amino acid sequence of a lipocalin different from hNGAL serves as "query sequence".

Given the above, a skilled artisan is thus readily in a position to determine which amino acid position mutated in hNGAL as described herein corresponds to an amino acid of a scaffold other than hNGAL. Specifically, a skilled artisan can align the amino acid sequence of a mutein as described herein, in particular an hNGAL mutein of the disclosure with the amino acid sequence of a different mutein to determine which amino acid(s) of said mutein correspond(s) to the respective amino acid(s) of the amino acid sequence of said different lipocalin. More specifically, a skilled artisan can thus determine which amino acid of the amino acid sequence of said different lipocalin corresponds to the amino acid at position(s) 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of hNGAL (SEQ ID NO: 1).

Proteins of present disclosure, which are directed against or specific for GPC3, include any number of specific-binding protein muteins that are based on a defined protein scaffold. As used herein, a "mutein," a "mutated" entity (whether protein or nucleic acid) or "mutant" refers to the exchange, deletion, or insertion of one or more nucleotides or amino acids, respectively, compared to the naturally occurring (wild-type) nucleic acid or protein "reference" scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or even more such as 21, 22, 23, 24, 25 and 26. However, it is preferred that a mutein of present disclosure is still capable of binding GPC3.

As used herein, a "lipocalin" is defined as monomeric protein of approximately 18-20 kDA in weight, having a cylindrical b-pleated sheet supersecondary structural region comprising a plurality of (preferably eight) b-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character. (Seem e.g., Flower D R., The lipocalin protein family: structure and function, Biochem J. 318:1-14 (1996); Flower D R., er al., The lipocalin protein family: structural and sequence overview. Biochim. Biophys. Acta 1482:9-24 (2000); Skerra, A. *Biochim. Biophys. Acta* 1482:337-350 (2000)). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

In a preferred embodiment, a protein of present disclosure is a mutein of lipocalin 2 (Lcn 2; also known as human neutrophil gelatinase-associated lipocalin, hNGAL, or as siderocalin). The terms "human neutrophil gelatinase-associated lipocalin", "hNGAL", "mature hNGAL", "lipocalin 2", "human lipocalin 2", "mature human lopcalin 2" and "Lcn2" are used interchangeably and refer to the mature hNGAL with the SWISS-PROT/UniProt Data Bank Accession Number P80188 (Isoform 1). The amino acid sequence shown in SWISS-PROT/UniProt Data Bank Accession Number P80188 is preferred as a "reference sequence".

Most preferred, the amino acid sequence shown in SEQ ID NO: 1 is preferred as a "reference sequence". SEQ ID NO: 1 shows the mature hNGAL. The terms "reference sequence" and "wild type sequence" are used interchangeably herein. The mature form of this protein has amino acids 21 to 198 of the complete sequence, since a signal peptide of amino acids 1-20 (MPLGLLWLGL ALLGALHAQA) is cleaved off. This protein further has a disulfide bond formed between the amino acid residues at positions 76 and 175 of the mature protein.

A mutein of the disclosure may include the wild type (natural) amino acid sequence of the "parental" protein scaffold (such as a lipocalin) outside the mutated amino acid sequence positions; alternatively, an hNGAL mutein may also contain amino acid mutations outside the sequence positions subjected to mutagenesis that do not interfere with the binding activity and the folding of the mutein. Such mutations can be accomplished on a DNA level using established standard methods (Sambrook, J. et al. *Molecular Cloning: A Laboratory Manual,* 3rd Ed., Cold Spring Harbor Laboratory Press, Cold Spring Harbor, N.Y. (2001).)

Possible alterations of the amino acid sequence are insertions or deletions as well as amino acid substitutions.

Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of a parental protein scaffold, where these deletions or insertion result in a stable folded/functional mutein, which can be readily tested by the skilled artisan.

The skilled artisan will appreciate methods useful to prepare protein muteins contemplated by the present disclosure but whose protein or nucleic acid sequences are not explicitly disclosed herein. As an overview, such modifications of the amino acid sequence include, e.g., directed mutagenesis of single amino acid positions in order to simplify sub-cloning of a mutated lipocalin gene or its parts by incorporating cleavage sites for certain restriction enzymes. In addition, these mutations can also be incorporated to further improve the affinity of a lipocalin mutein for a given target. Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

Accordingly, the present disclosure also includes functional variants of proteins disclosed herein, which have a threshold sequence identity or sequence homology to a reference protein. By "identity" or "sequence identity" is meant a property of sequences that measures their similarity or relationship. The term "sequence identity" or "identity" as used in the present disclosure means the percentage of pair-wise identical residues—following (homologous) alignment of a sequence of a polypeptide of present disclosure with a sequence in question—with respect to the number of residues in the longer of these two sequences. Percent identity is determined by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of two proteins.

The percentage of sequence homology or sequence identity can, for example, be determined herein using the program BLASTP, version blastp 2.2.5 (Nov. 16, 2002). Cf. Altschul, S. F. et al. *Nucl. Acids Res.* 25, 3389-3402 (1997).). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

It is also possible to deliberately mutate other amino acid sequence positions to cysteine in order to introduce new reactive groups, for example, for the conjugation to other compounds, such as polyethylene glycol (PEG), hydroxy-ethyl starch (HES), biotin, peptides or proteins, or for the formation of non-naturally occurring disulphide linkages. With respect to a mutein of human lipocalin 2, exemplary possibilities of such a mutation to introduce a cysteine residue into the amino acid sequence of a lipocalin including human lipocalin 2 mutein to include the introduction of a cysteine (Cys) residue at at least at one of the sequence positions that correspond to sequence positions 14, 21, 60, 84, 88, 116, 141, 145, 143, 146 or 158 of the wild type sequence of hNGAL. In some embodiments where a human lipocalin 2 mutein of present disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human lipocalin 2 mutein.

In some preferred embodiments, a mutein according to the disclosure binds human or mouse GPC3 with a $K_D$ of about 1 nM or less, including 0.5 nM or less, 0.3 nM or less, and or 0.2 nM or less. A mutein of the disclosure may specifically bind one or more continuous, discontinuous or conformation epitope(s) of the mature, folded bioactive form of GPC3.

The binding affinity of a protein of present disclosure (e.g. a mutein of a lipocalin) to a selected target (in the present case, GPC3), can be measured (and thereby $K_D$ values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

The amino acid sequence of a mutein of the disclosure may have a high sequence identity to mature human lipocalin 2. In this context, a protein of present disclosure may have at least 70%, at least 75%, at least 80%, at least 82%, at least 85%, at least 87%, at least 90% identity, including at least 95% identity to a protein selected from the group consisting of the sequence of SEQ ID NO: 1 such a mutein of an amino acid sequence selected from the group consisting of SEQ ID NOs: 5-16.

The disclosure also includes structural homologues of the proteins selected from the group consisting of the sequence of SEQ ID NOs: 5-16, which have an amino acid sequence homology or sequence identity of more than about 60%, preferably more than 65%, more than 70%, more than 75%, more than 80%, more than 85%, more than 90%, more than 92% and most preferably more than 95% in relation thereto.

The terms "Glypican-3, "glypican proteoglycan 3," "GPC3," "OTTHUMP00000062492", "GTR2-2" "SGB," "DGSX", "SDYS", "SGBS", "OCI-5", and "SGBSI" are used interchangeably, and include variants, isoforms and species homologs of human Glypican-3. The complete amino acid sequence of an exemplary human Glypican-3 has Genbank/NCBI accession number NM_004484.

In line with the above, a mutein of the disclosure preferably acts as an antagonist of GPC3. In some embodiments, a mutein of the disclosure may act as an antagonist of GPC3 by inhibiting the ability of the GPC3 molecule to bind to or otherwise interact with its cognate ligand.

In yet another aspect, the present disclosure includes muteins of human lipocalin 2 that specifically bind GPC3. In this sense, GPC3 can be regarded a non-natural ligand of wild type human lipocalin 2, where "non-natural ligand" refers to a compound that does not bind to human lipocalin 2 under physiological conditions. By engineering wildtype lipocalins such as human lipocalin 2 with mutations at certain positions, the present inventors have demonstrated that high affinity and high specificity for a non-natural ligand is possible. In one aspect at least at 1, 2, 3, 4, 5, 6, 7, 8, 9, 10, 11, 12, 13, 14, 15, 16, 17, 18, 19, and/or 20 nucleotide triplet(s) encoding for any of the sequence positions 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of a mature human lipocalin 2 (SEQ ID NO: 1), a random mutagenesis can be carried out by allowing substitution at these positions by a subset of nucleotide triplets.

Further, the lipocalins can be used to generate muteins that have a mutated amino acid residue at any one or more, including at least at any two, three, four, five, six, seven, eight, nine, ten, eleven, twelve, thirteen, fourteen, fifteen, sixteen, seventeen, eighteen, nineteen or twenty, of the sequence positions of the sequence positions corresponding to the sequence positions 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of a mature human lipocalin 2 (SEQ ID NO: 1).

A substitution at sequence position 36 may for example be a substitution Leu 36→Val or Arg. A substitution at sequence position 40 may for example be a substitution Ala 40→Leu, Val or Gly. A substitution at sequence position 41 may for example be a substitution Ile 41→Leu, Arg, Met, Gly or Ala. A substitution at sequence position 49 may for example be a substitution Gln 49→Pro or Leu. A substitution at sequence position 52 may for example be a substitution Tyr 52→Arg or Trp. A substitution at sequence position 68 may for example be a substitution Asn 65→Asp. A substitution at sequence position 68 may for example be a substitution Ser 68→Val, Gly, Asn or Ala. A substitution at sequence position 70 may for example be a substitution Leu 70→Arg, Ser, Ala or Val. A substitution at sequence position 72 may for example be a substitution Arg 72→Asp, Trp, Ala, or Gly. A substitution at sequence position 73 may for example be a substitution Lys 73→Gly, Arg, Asn, Glu or Ser. A substitution at sequence position 76 may for example be a substitution Cys 76→Val or Ile. A substitution at sequence position 77 may for example be a substitution Asp 77→His, Met, Val, Leu, Thr or Lys. A substitution at sequence position 79 may for example be a substitution Trp 79→Lys, Ser or Thr. A substitution at sequence position 81 may for example be a substitution Arg 81→Gly. A substitution at sequence position 81 may for example be a substitution Cys 87→Ser. A substitution at sequence position 96 may for example be a substitution Asn 96→Arg, Asp, Gln or Pro. A substitution at sequence position 100 may for example be a substitution Tyr 100→Gly, Glu, Pro or Gln. A substitution at sequence position 103 may for example be a substitution Leu 103→Glu, Gln, Asn, Gly, Ser or Tyr. A substitution at sequence position 106 may for example be a substitution Ser 105→Ala. A substitution at sequence position 106 may for example be a substitution Tyr 106→Asn, Ser or Thr. A substitution at sequence position 125 may for example be a substitution Lys 125→Glu. A substitution at sequence position 127 may for example be a substitution Ser 127→Arg or Tyr. A substitution at sequence position 132 may for example be a substitution Tyr 132→Trp or Ile. A substitution at sequence position 134 may for example be a substitution Lys 134→Ala or Phe. A substitution at sequence position 134 may for example be a substitution Thr 136→Ile. A substitution at sequence position 175 may for example be a substitution Cys 175→Ala. Noteworthy, any of the amino acids that substitute the corresponding amino acid in the reference sequence can be exchanged by a corresponding conservative amino acid. In particular, conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

In one embodiment, a mutein of present disclosure, which binds to GPC3 includes the following amino acid replacements:

(a) Leu 36→Val; Ile 41→Leu; Gln 49→Leu; Tyr 52→Arg; Asn 65→Asp; Ser 68→Val; Leu 70→Ser; Arg 72→Trp; Lys 73→Arg; Asp 77→His; Trp 79→Lys; Arg 81→Gly; Cys 87→Ser; Asn 96→Asp; Tyr 100→Gly; Leu 103→Gln; Tyr 106→Asn; Lys 125→Glu; Ser 127→Arg; Tyr 132→Trp; Lys 134→Ala;

(b) Leu 36→Val; Ala 40→Val; Ile 41→Arg; Gln 49→Pro; Tyr 52→Arg; Asn 65→Asp; Ser 68→Gly; Leu 70→Ser; Lys 73→Gly; Asp 77→His; Trp 79→Lys; Arg 81→Gly; Cys 87→Ser; Asn 96→Asp; Tyr 100→Gly; Leu 103→Glu; Tyr 106→Asn; Lys 125→Glu; Ser 127→Arg; Tyr 132→Trp; Lys 134→Phe;

(c) Leu 36→Val; Ala 40→Gly; Ile 41→Met; Gln 49→Leu; Tyr 52→Arg; Asn 65→Asp; Leu 70→Ala; Lys 73→Asn; Asp 77→His; Trp 79→Lys; Arg 81→Gly; Cys 87→Ser; Asn 96→Gln; Tyr 100→Gly; Leu 103→Glu; Tyr 106→Asn; Lys 125→Glu; Ser 127→Arg; Tyr 132→Trp; Lys 134→Phe;

(d) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Arg; Asp 77→Leu; Trp 79→Ser; Arg 81→Gly; Cys 87→Ser; Asn 96→Gln; Tyr 100→Glu; Leu 103→Asn; Ser 105→Ala; Tyr 106→Asn; Lys 125→Glu; Ser 127→Tyr; Tyr 132→Ile; Lys 134→Phe; Thr 136→Ile;

(e) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Arg; Asp 77→Thr; Trp 79→Ser; Arg 81→Gly; Cys 87→Ser; Asn 96→Gln; Tyr 100→Glu; Leu 103→Gly; Ser 105→Ala; Tyr 106→Asn; Lys 125→Glu; Ser 127→Tyr; Tyr 132→Ile; Lys 134→Phe; Thr 136→Ile;

(f) Leu 36→Arg; Ala 40→Gly; Ile 41→Ala; Gln 49→Pro; Tyr 52→Trp; Asn 65→Asp; Ser 68→Asn; Leu 70→Arg; Arg 72→Ala; Lys 73→Arg; Asp 77→Val; Trp 79→Ser; Arg 81→Gly; Cys 87→Ser; Asn 96→Pro; Tyr 100→Glu; Leu 103→Asn; Ser 105→Ala; Tyr 106→Ser; Lys 125→Glu; Ser 127→Tyr; Tyr 132→Ile; Lys 134→Phe; Thr 136→Ile;

(g) Leu 36→Arg; Ala 40→Val; Ile 41→Ala; Gln 49→Pro; Tyr 52→Arg; Asn 65→Asp; Ser 68→Ala; Leu 70→Arg; Arg 72→Ala; Lys 73→Arg; Asp 77→Leu; Trp 79→Ser; Arg 81→Gly; Cys 87→Ser; Asn 96→Arg; Tyr 100→Glu; Leu 103→Tyr; Ser 105→Ala; Tyr 106→Asn; Lys 125→Glu; Ser 127→Tyr; Tyr 132→Ile; Lys 134→Phe; Thr 136→Ile;

(h) Leu 36→Arg; Ala 40→Val; Ile 41→Ala; Gln 49→Pro; Tyr 52→Arg; Asn 65→Asp; Ser 68→Asn; Leu 70→Val; Arg 72→Ala; Lys 73→Gly; Asp 77→Lys; Trp 79→Ser; Arg 81→Gly; Cys 87→Ser; Asn 96→Arg; Tyr 100→Pro; Leu 103→Asn; Ser 105→Ala; Tyr 106→Asn; Lys 125→Glu; Ser 127→Tyr; Tyr 132→Ile; Lys 134→Phe; Thr 136→Ile;

(i) Leu 36→Arg; Ala 40→Leu; Ile 41→Gly; Gln 49→Pro; Tyr 52→Trp; Asn 65→Asp; Ser 68→Asn; Leu 70→Arg; Arg 72→Ala; Lys 73→Arg; Asp 77→Met; Trp 79→Ser; Arg 81→Gly; Cys 87→Ser; Asn 96→Gln; Tyr 100→Glu; Leu 103→Ser; Ser 105→Ala; Tyr 106→Asn; Lys 125→Glu; Ser 127→Tyr; Tyr 132→Ile; Lys 134→Phe;

(j) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Gly; Cys 76→Val; Asp 77→Lys; Trp 79→Thr; Arg 81→Gly; Cys 87→Ser; Asn 96→Gln; Tyr 100→Glu; Leu 103→Asn; Ser 105→Ala; Tyr 106→Thr; Lys 125→Glu; Ser 127→Tyr; Tyr 132→Ile; Lys 134→Phe; Cys 175→Ala;

(k) Leu 36→Arg; Ala 40→Val; Ile 41→Gly; Gln 49→Pro; Tyr 52→Arg; Asn 65→Asp; Ser 68→Gly; Leu 70→Arg; Arg 72→Gly; Lys 73→Glu; Cys 76→Ile; Asp 77→Lys; Trp 79→Ser; Arg 81→Gly; Cys 87→Ser; Asn 96→Gln; Tyr 100→Gln; Leu 103→Asp; Ser 105→Ala; Tyr 106→Thr; Lys 125→Glu; Ser 127→Tyr; Tyr 132→Ile; Lys 134→Phe; Thr 136→Ile; Cys 175→Ala; or (l) Leu 36→Arg; Ala 40→Val; Ile 41→Gly; Gln 49→Pro; Tyr 52→Arg; Asn 65→Asp; Ser 68→Gly; Leu 70→Arg; Arg 72→Asp; Lys 73→Ser; Cys 76→Val; Asp 77→Thr; Trp 79→Ser; Arg 81→Gly; Cys 87→Ser; Asn 96→Gln; Tyr 100→Glu; Leu 103→Asn; Ser 105→Ala; Tyr 106→Thr; Lys 125→Glu; Ser 127→Tyr; Tyr 132→Ile; Lys 134→Phe; Thr 136→Ile; Cys 175→Ala.

The numbering is preferably in relation to the linear polypeptide sequence of mature hNGAL (SEQ ID NO: 1). Accordingly, given the teaching of the disclosure, a skilled artisan can readily determine which amino acids in the preferred reference sequence of mature hNGAL (SEQ ID NO: 1) correspond to those described above in (a) to (l); so as to mutate said amino acids in the reference sequence.

In some particular embodiments, a mutein according to the disclosure binds human or mouse GPC3 with a stronger binding affinity than the mutein of SEQ ID NO: 3 and/or the mutein of SEQ ID NO: 4, for example, such mutein may have a lower $K_D$ value than that of the mutein of SEQ ID NO: 3 or 4 when measured by Surface plasmon resonance (SPR) analysis as essentially described in Example 4.

In some still further embodiments, a mutein according to the disclosure exhibit improved EC50 value compared to the mutein of SEQ ID NO: 3 and/or the mutein of SEQ ID NO: 4, for example, such mutein may have a lower nM than that of the mutein of SEQ ID NO: 3 or 4 when measured by an assay based on SK-HEP-1 cells transfected with human, mouse or cynomolgus GPC3 as essentially described in Example 5.

In some additional embodiments, a mutein of the disclosure is more biophysically stable than the mutein of SEQ ID NO: 3 and/or the mutein of SEQ ID NO: 4, for example, when such mutein may have increased melting temperature compared to the mutein of SEQ ID NO: 3 or 4 measured by a fluorescence-based thermal denaturation assay as essentially described in Example 6.

It is also noted that the complex formation between the respective mutein and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

In one embodiment, the muteins disclosed herein can be linked, either N- or C-terminal to a fusion partner which is preferably a protein, or a protein domain or a peptide. Examples of a fusion partner is an affinity tag such as pentahistidine tag, a hexahistidine tag or a steptavidin tag (e.g.) Streptag®. Thus, the present application encompasses also all explicitly and generic described muteins equipped with such tags.

The term "fragment" as used in the present disclosure in connection with the feature lipocalin mutein fragment relates to proteins or peptides derived from full-length mature Lcn 2 that are N-terminally and/or C-terminally shortened, i.e. lacking at least one of the N-terminal and/or C-terminal amino acids. Such fragments include preferably at least 10, more preferably 20, most preferably 30 or more consecutive amino acids of the primary sequence of mature Lcn 2 and are usually detectable in an immunoassay of mature Lcn 2. The word "detect" or "detecting" as used herein is understood both on a quantitative and a qualitative level, as well as a combination thereof. It thus includes quantitative, semi-quantitative and qualitative measurements of a molecule of interest. Accordingly, the presence or absence of a molecule such as GPC3, e.g. in a sample, as well as its concentration or level may be determined.

Also included in the scope of the present disclosure are the above muteins, which have been altered with respect to their immunogenicity, to reduce any detected immunogenicity by employing methods known to the skilled person in the field.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. To reduce the immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class I molecules. (Altuvia et al., J. Mol. Biol. 249:244-250 (1995).). Such an approach may also be utilized to identify potential T-cell epitopes in the muteins of present disclosure and to make, depending on its intended use, a selection of a specific mutein on the basis of its predicted immunogenicity. It may be furthermore possible to subject peptide regions that have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al., Hybridoma 19(6): 463-471 (2000)) and may be adapted to the muteins of the present disclosure. The muteins thus obtained may possess a minimized immunogenicity, which is desirable for their use in therapeutic and diagnostic applications, such as those described below.

For some applications, it is also useful to employ the muteins of present disclosure in a conjugated form. The conjugation can be carried out using any conventional coupling method known in the art.

The term "organic molecule" or "small organic molecule" as used herein for the non-natural target denotes an organic molecule comprising at least two carbon atoms, preferably not more than 7 or 12 rotatable carbon bonds, having a molecular weight in the range between 100 and 2000 daltons, preferably between 100 and 1000 daltons, and optionally including one or two metal atoms.

In general, it is possible to label a lipocalin mutein described herein with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation. Alkaline phosphatase, horseradish peroxidase or β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present disclosure. The muteins of present disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). Examples of suitable toxins include, but are not limited to pertussis-toxin, diphtheria toxin, ricin, saporin, pseudomonas exotoxin, calicheamicin or a derivative thereof, a taxoid, a maytansinoid, a tubulysin or a dolastatin analogue. The dolastatin analogue may be auristatin E, monomethylauristatin E, auristatin PYE and auristatin PHE. Examples of cytostatic agent include, but are not limited to Cisplatin, Carboplatin, Oxaliplatin, 5-Fluorouracil, Taxotere (Docetaxel), Paclitaxel, Anthracycline (Doxorubicin), Methotrexate, Vinblastin, Vincristine, Vindesine, Vinorelbine, Dacarbazine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, methoxyestradiol derivatives and leucovorin. The lipocalin muteins of present disclosure may also be conjugated with therapeutically active nucleic acids such as antisense nucleic acid molecules, small interfering RNAs, micro RNAs or ribozymes. Such conjugates can be produced by methods well known in the art.

In one embodiment, the muteins of present disclosure may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the muteins of present disclosure may be coupled to moieties that facilitate the active transport across this barrier. (Gaillard P J, et al., International Congress Series. 127:185-

198 (2005); Gaillard P J, et al., Expert Opin Drug Deliv. 2(2):299-309 (2005).) Such compounds are for example available under the trade name 2B-Trans™ (to-BBB technologies BV, Leiden, NL). Other exemplary targeting molecules to which the muteins of the present disclosure may be coupled include antibodies, antibody fragments or lipocalin muteins with affinity for a desired target molecule. The target molecule of the targeting moieties may, for example, be a cell-surface antigen. Cell-surface antigens may be specific for a cell or tissue type, such as, for example, cancer cells. Illustrative examples of such cell surface proteins are HER-2 or proteoglycans such as NEU-2.

As indicated above, a mutein of present disclosure may in some embodiments be conjugated to a compound that extends the serum half-life of the mutein (in this regard see also PCT Publication No. WO2006/56464 where such conjugation strategies are described with references to muteins of human neutrophil gelatinase-associated lipocalin with binding affinity for CTLA-4). The compound that extends the serum half-life may be a polyalkylene glycol molecule, such as polyethylene ("PEG") or an activated derivative thereof; hydroxyethyl starch, fatty acid molecules, such as palmitic acid (Vajo & Duckworth *Pharmacol. Rev.* 52:1-9 (2000)), an Fc part of an immunoglobulin, a $C_H3$ domain of an immunoglobulin, a $C_H4$ domain of an immunoglobulin, albumin or a fragment thereof, an albumin binding peptide, an albumin binding protein, transferrin, or the tag Pro-Ala-Ser, to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation compounds for extending the half-life of a lipocalin mutein of present disclosure include albumin (Osborn et al., J. Pharmacol. Exp. Ther. 303:540-548 (2002)), or an albumin binding protein, for example, a bacterial albumin binding domain, such as the one of streptococcal protein G. (Konig, T. and Skerra, A., J. Immunol. Methods 218:73-83 (1998).) Other examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in US Patent Application Publication No. 2003/0069395 or Dennis et al. (Dennis et al., J. Biol. Chem. 277:35035-35043 (2002)).

In other embodiments, albumin itself or a biological active fragment of albumin can be used as compound of a lipocalin mutein of present disclosure that extends the serum half-life of the mutein. The term "albumin" includes all mammal albumins such as human serum albumin or bovine serum albumin or rat albumin. The albumin or fragment thereof can be recombinantly produced as described in U.S. Pat. No. 5,728,553 or European Patent Application Nos. EP 0 330 451 and EP 0 361 991. Recombinant human albumin (Recombumin®) for use as a protein stabilizer is for example available from Novozymes Delta Ltd. (Nottingham, UK).

If the albumin-binding protein is an antibody fragment it may be a domain antibody. Domain antibodies (dAbs) are engineered to allow precise control over biophysical properties and in vivo half-life to create the optimal safety and efficacy product profile. Domain antibodies are for example commercially available from Domantis Ltd. (Cambridge, UK and MA, USA).

Using transferrin as a moiety to extend the serum half-life of the muteins of present disclosure, the muteins can be genetically fused to the N- or C-terminus, or both, of non-glycosylated transferrin. Non-glycosylated transferrin has a half-life of 14 to 17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer is also commercially available from Novozymes Delta Ltd. (Nottingham, UK).

If an Fc part of an immunoglobulin is used for the purpose to prolong the serum half-life of the muteins of present disclosure, the SynFusion™ technology, commercially available from Syntonix Pharmaceuticals, Inc (MA, USA), may be used. The use of this Fc-fusion technology allows the creation of longer-acting biopharmaceuticals and may for example comprise two copies of the mutein linked to the Fc region of an antibody to improve pharmacokinetics, solubility, and production efficiency.

Yet another alternative to prolong the half-life of a mutein of present disclosure is to fuse the N- or C-terminus of a mutein of present disclosure to long, unstructured, flexible glycine-rich sequences (for example poly-glycine with about 20 to 80 consecutive glycine residues). This approach disclosed in PCT Publication No. WO2007/038619, for example, has also been termed "rPEG" (recombinant PEG).

If polyalkylene glycol is used as compound that extends the half-life of the mutein, the polyalkylene glycol can be substituted or unsubstituted. It can also be an activated polyalkylene derivative. Examples of suitable compounds are polyethylene glycol (PEG) molecules as described in WO99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase. (See, e.g., Fuertges et al., The Clinical Efficacy of Poly (Ethylene Glycol)-Modified Proteins, J. Control. Release 11:139-148 (1990).) The molecular weight of such a polymer, preferably polyethylene glycol, may range from about 300 to about 70,000 daltons, including, for example, polyethylene glycol with a molecular weight of about 10,000, of about 20,000, of about 30,000 or of about 40,000 dalton. Moreover, e.g. as described in U.S. Pat. No. 6,500,930 or 6,620,413, carbohydrate oligo- and polymers such as starch or hydroxyethyl starch ("HES") can be conjugated to a mutein of present disclosure for the purpose of serum half-life extension.

In another embodiment, in order to provide suitable amino acid side chains for conjugating one of the above compounds to the muteins of present disclosure artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

For several applications of the muteins disclosed herein, it may be advantageous to use them in the form of fusion proteins. In some embodiments, the inventive mutein is fused at its N-terminus and/or it's C-terminus to a protein, a protein domain or a peptide such as a signal sequence and/or an affinity tag.

For pharmaceutical applications, a mutein of present disclosure may be fused to a fusion partner that extends the in vivo serum half-life of the mutein (see again PCT Publication No. WO2006/56464 where suitable fusion partner are described with references to muteins of human neutrophile gelatinase-associated lipocalin with binding affinity for CTLA-4). Similar to the conjugated compounds described above, the fusion partner may be an Fc part of an immunoglobulin, a $C_H3$ domain of an immunoglobulin, a $C_H4$ domain of an immungloubulin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of present disclosure include albumin (Osborn, B. L. et al. supra *J. Pharmacol. Exp. Ther.* 303:540-548 (2002)), or an albumin binding protein, for example, a bacterial albumin binding domain, such as streptococcal protein G (Konig, T. and Skerra, A. *J. Immunol. Methods* 218:73-83 (1998)). The albumin binding peptides described in Dennis et al, supra (2002) or US Patent Application Publication No. 2003/0069395 having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner. It is also possible to use albumin itself or a biological active fragment of albumin as fusion partner of a lipocalin mutein of present disclosure. The term "albumin" includes all mammal albumins such as human serum albumin or bovine serum albumin or rat serum albumin. The recombinant production of albumin or fragments thereof is well known in the art and for example described in U.S. Pat. No. 5,728,553, European Patent Application Nos. EP 0 330 451 or EP 0 361 991.

The fusion partner may confer new characteristics to the inventive lipocalin mutein such as enzymatic activity or binding affinity for other molecules. Examples of suitable fusion proteins are alkaline phosphatase, horseradish peroxidase, gluthation-S-transferase, the albumin-binding domain of protein G, protein A, antibody fragments, oligomerization domains, lipocalin muteins of same or different binding specificity (which results in the formation of "duocalins," cf. Schlehuber, S., and Skerra, A., Duocalins, engineered ligand-binding proteins with dual specificity derived from the lipocalin fold (*Biol. Chem.* 382:1335-1342 (2001)), or toxins.

In particular, it may be possible to fuse a lipocalin mutein of present disclosure with a separate enzyme active site such that both "components" of the resulting fusion protein together act on a given therapeutic target. The binding domain of the lipocalin mutein attaches to the disease-causing target, allowing the enzyme domain to abolish the biological function of the target.

Affinity tags such as the Strep-tag® or Strep-tag® II (Schmidt, T. G. M. et al., J. Mol. Biol. 255:753-766 (1996)), the myc-tag, the FLAG-tag, the $His_6$-tag or the HA-tag or proteins such as glutathione-S-transferase also allow easy detection and/or purification of recombinant proteins are further examples of preferred fusion partners. Finally, proteins with chromogenic or fluorescent properties such as the green fluorescent protein ("GFP") or the yellow fluorescent protein ("YFP") are suitable fusion partners for a lipocalin mutein of present disclosure as well.

The term "fusion protein" as used herein also includes lipocalin muteins according to present disclosure containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences are known in the art. A preferred signal sequence for secretion a polypeptide into the periplasm of *E. coli* is the OmpA-signal sequence.

The present disclosure also relates to nucleic acid molecules (DNA and RNA) comprising nucleotide sequences coding for muteins as described herein. Since the degeneracy of the genetic code permits substitutions of certain codons by other codons specifying the same amino acid, present disclosure is not limited to a specific nucleic acid molecule encoding a mutein of present disclosure but includes all nucleic acid molecules comprising nucleotide sequences encoding a functional mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements that contain information regarding transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of present disclosure can include a regulatory sequence, preferably a promoter sequence. In another preferred embodiment, a nucleic acid molecule of present disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of present disclosure can also be part of a vector or any other kind of cloning vehicle, such as a plasmid, a phagemid, a phage, a baculovirus, a cosmid or an artificial chromosome such as a YAC or BAC.

The DNA molecule encoding lipocalin muteins of present disclosure, and in particular a cloning vector containing the coding sequence of such a lipocalin mutein can be transformed into a host cell capable of expressing the gene. Transformation can be performed using standard techniques. (Sambrook, J. et al. (2001), supra.)

Thus, the present disclosure is also directed to a host cell containing a nucleic acid molecule as disclosed herein.

The present disclosure also relates to a method for the production of a mutein of the present disclosure, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then enriched, purified or isolated from this host organism or its culture. It is also possible to produce a protein in vitro, for example by use of an in vitro translation system. The term "enriched" means that the mutein or a functional fragment thereof constitutes a significantly higher fraction of the total protein present in a sample or solution of interest than in a sample or solution from which it was taken. Enrichment may for instance include the isolation of a certain fraction from a cell extract. This may be obtained by standard techniques such as centrifugation. Examples of other means of enrichment are filtration or dialysis, which may for instance be directed at the removal of undesired molecules below a certain molecular weight, or a precipitation using organic solvents or ammonium sulphate. Purification may for instance include a chromatographic technique, for example gel filtration, ion exchange chromatography, affinity purification, hydrophobic interaction chromatography or hydrophobic charge induction chromatography. Another example for a purification is an electrophoretic technique, such as preparative capillary electrophoresis. Isolation may include the combination of similar methods. As used herein, "substantially pure" or "substantially purified" means a compound or species that is the predominant species present (i.e., on a molar basis it is more abundant than any other individual species in the composition). In some embodiments, a substantially purified composition is a composition in which the species includes at least about 50 percent (on a molar basis) of all molecular or, as applicable, all macromolecular species present. In certain embodiments, a substantially pure composition will have more than about 80%, about 85%, about 90%, about 95%, or about 99% of all molecular or, as applicable, all macromolar species present in the composition.

When producing the mutein in vivo, a nucleic acid encoding a mutein of present disclosure is introduced into a suitable bacterial or eukaryotic host organism by means of recombinant DNA technology (as already outlined above). For this purpose, the host cell is first transformed with a cloning vector comprising a nucleic acid molecule encoding a mutein of present disclosure using established standard methods. (Sambrook, J. et al. Molecular cloning: a laboratory manual (1989).) The host cell is then cultured under conditions, which allow expression of the heterologous DNA and thus the synthesis of the corresponding polypeptide. Subsequently, the polypeptide is recovered either from the cell or from the cultivation medium.

In one aspect, the present disclosure relates to a method for the generation of a mutein which binds GPC3, comprising:

subjecting a nucleic acid molecule encoding a lipocalin to mutagenesis, resulting in one or more mutein nucleic acid molecule(s).

The method can further include:
expressing the one more mutein nucleic acid molecule(s) obtained in (a) in a suitable expression system,
bringing the plurality of muteins into contact with at least a fragment or a mature form of GPC3, and
enriching the one or more mutein(s) having a detectable binding affinity for a given target by means of selection and/or isolation.

The term "mutagenesis" as used herein means that the experimental conditions are chosen such that the amino acid naturally occurring at a given sequence position of the lipocalin, including hNGAL can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of present disclosure that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in present disclosure. In one exemplary embodiment of present disclosure, an insertion of several mutations may be introduced into the loop AB of the chosen lipocalin scaffold (cf. PCT Publication No. WO2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

In one non-limiting approach, the coding sequence of human lipocalin 2 can be used as a starting point for the mutagenesis of the peptide segments selected in the present disclosure. For the mutagenesis of the recited amino acid positions, the person skilled in the art has at his disposal the various established standard methods for site-directed mutagenesis. (Sambrook, J. et al. (2001), supra.) A commonly used technique is the introduction of mutations by means of PCR (polymerase chain reaction) using mixtures of synthetic oligonucleotides, which bear a degenerate base composition at the desired sequence positions. Other similar techniques are well known to those of skill in the art.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning. (Sambrook, J. et al. (2001), supra.) For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

In a further embodiment, the method includes subjecting the nucleic acid molecule to mutagenesis at nucleotide triplets coding for at least any 1, 2, 3, 4, 5, 6, 7, 8, 9, 10, 11, 12, 13, 14, 15, 16, 17, 18, 19, 20 or even more of the sequence positions corresponding to the sequence positions 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of the lipocalin, in particular of the linear polypeptide sequence of mature hNGAL (SEQ ID NO: 1). Such a nucleic acid may be subjected to mutagenesis and introduced into a suitable bacterial or eukaryotic host organism by using recombinant DNA technology. Obtaining a nucleic acid library of a lipocalin can be carried out using any suitable technique that is known in the art for generating lipocalin muteins with antibody-like properties, i.e. muteins that have affinity towards a given target. Examples of such combinatorial methods are described in detail in the PCT Application Nos. WO99/16873, WO00/75308, WO03/029471, WO03/029462, WO03/029463, WO2005/019254, WO 2005/019255, WO 2005/019256, or WO 2006/56464 for instance. The content of each of these patent applications is incorporated herein by reference in their entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (Adey, N B et al., Identification of calmodulin-binding peptide consensus sequences from a phage-displayed random peptide library, Gene 169:133-4 (1996) (1996); Lowman, H. B., Bacteriophage display and discovery of peptide leads for drug development Annu Rev Biophys Biomol Struct. 26:401-24 (1997); Rodi D J et al., Phage-display technology—finding a needle in a vast molecular haystack *Curr Opin Biotechnol.* 10(1):87-93 (1999)), colony screening (reviewed in Pini, A. et al., Comb. Chem. High Throughput Screen. 5:503-510 (2002)), ribosome display (reviewed in Amstutz, P. et al. *Curr. Opin. Biotechnol.* 12:400-405 (2001)) or mRNA display as reported in Wilson, D. S. et al., Proc. Natl. Acad. Sci. USA 98:3750-3755 (2001) or the methods specifically described in PCT Publication Nos. WO99/16873, WO00/75308, WO03/029471, WO03/029462, WO03/029463, WO2005/019254, WO2005/019255, WO2005/019256, or WO2006/56464.

In accordance with this disclosure, another embodiment of the above methods comprises:
providing at least a fragment of GPC3 as a given target/ligand for example,
contacting the plurality of muteins with said target/ligand in order to allow formation of complexes between said ligand and muteins having binding affinity for said target/ligand, and
removing muteins having no or no substantial binding affinity.

In one embodiment of the methods of present disclosure, the selection binding affinity is carried out under competitive conditions. Competitive conditions as used herein means that selection of muteins encompasses at least one step in which the muteins and the fragment of GPC3 are brought in contact in the presence of an additional ligand, which competes with binding of the muteins to the target, GPC3. Alternatively, the additional ligand competes with binding of the muteins by complexing an epitope distinct from the binding site of the muteins to the target by allosteric effects. Accordingly, any fragment, precursor or mature form of GPC3 can be used in the generation of muteins of present disclosure.

A further embodiment of the methods of present disclosure involves operably fusing a nucleic acid coding for the plurality of muteins of present disclosure and resulting from mutagenesis at the 3' end with a gene coding for the coat protein pIII of a filamentous bacteriophage of the M13-family or for a fragment of this coat protein, in order to select at least one mutein for the binding of a given ligand.

The fusion protein may include additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

The inventive nucleic acid molecules coding for muteins of present disclosure can be inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

Once a mutein with affinity to a given target has been selected, it is additionally possible to subject such a mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation," can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al., J. Mol. Biol. 255:589-603 (1996). Other methods of random mutagenesis that are suitable for such purposes include random insertion/deletion (RID) mutagenesis as described by Murakami et al., Nat. Biotechnol. 20:76-81 (2002) or nonhomologous random recombination (NRR) as described by Bittker et al., Nat. Biotechnol. 20:1024-1029 (2002). If desired, affinity maturation can also be carried out according to the procedure described in PCT Publication No. WO00/75308 or Schlehuber et al., J. Mol. Biol. 297:1105-1120 (2000), where muteins of the bilin-binding protein having high affinity to digoxigenin were obtained. A further approach for improving the affinity is to carry out positional saturation mutagenesis. In this approach "small" nucleic acid libraries can be created in which amino acid exchanges/mutations are only introduced at single positions within any of the four loop segments. These libraries are then directly subjected to a selection step (affinity screening) without further rounds of panning. This approach allows the identification of residues that contribute to improved binding of the desired target and allows identification of "hot spots" that are important for the binding.

In one embodiment, the above method for modifying a mutein further includes introducing a Cys residue at at least one of any of the sequence positions that correspond to sequence positions 14, 21, 60, 84, 88, 116, 141, 145, 143, 146 or 158 of the wild type sequence of human lipocalin 2 and coupling a moiety that is able to modify the serum half time of said mutein via the thiol group of a Cys residue introduced at at least one of any of the sequence positions that correspond to sequence positions 14, 21, 60, 84, 88, 116, 141, 145, 143, 146 or 158 of the wild type sequence of hNGAL. The moiety that is able to modify the serum half time of said mutein may be selected from the group consisting of a polyalkylene glycol molecule and hydroxyethylstarch.

Where a protein of present disclosure is a human lipocalin 2 mutein of present disclosure, the naturally occurring disulfide bond between Cys 76 and Cys 175 may be removed. Accordingly, such muteins (or any other human lipocalin 2 mutein that does not include an intramolecular disulfide bond) can be produced in a cell compartment having a reducing redox milieu, for example, in the cytoplasma of Gram-negative bacteria.

In case a lipocalin mutein of present disclosure includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a mutein of present disclosure in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol. (Venturi et al., J. Mol. Biol. 315:1-8 (2002).)

However, a mutein of present disclosure may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (reviewed, e.g., in Lloyd-Williams et al. *Chemical Approaches to the Synthesis of Peptides and Proteins*, CRC Press, Boca Raton, Fields, G B, (1997); Colowick *Solid-Phase Peptide Synthesis*. Academic Press, San Diego (1997); Bruckdorfer et al., Curr. Pharm. Biotechnol. 5:29-43 (2004)).

In another embodiment, the muteins of present disclosure may be produced by in vitro transcription/translation employing well-established methods known to those skilled in the art.

The present disclosure also relates to a pharmaceutical composition that includes at least one inventive mutein referred to in the claims or a fusion protein or conjugates thereof and, optionally, a pharmaceutically acceptable excipient.

The lipocalin muteins according to present disclosure can be administered via any parenteral or non-parenteral (e.g. enteral) route that is therapeutically effective for proteinaceous drugs. Parenteral application methods include, for example, intracutaneous, subcutaneous, intramuscular or intravenous injection and infusion techniques, e.g. in the form of injection solutions, infusion solutions or tinctures, as well as aerosol installation and inhalation, e.g. in the form of aerosol mixtures, sprays or powders. Non-parenteral delivery modes are, for instance, orally, e.g. in the form of pills, tablets, capsules, solutions or suspensions, or rectally, e.g. in the form of suppositories. The muteins of present disclosure can be administered systemically or topically in formulations containing conventional non-toxic pharmaceutically acceptable excipients or carriers, additives and vehicles as desired.

In one embodiment of the present disclosure the pharmaceutical is administered parenterally to a vertebrate animal, including a mammal, and in particular to a human. Corresponding administration methods include, but are not limited to, for example, intracutaneous, subcutaneous, intramuscular or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan and Michniak, Am. J. Ther. 11(4):312-316 (2004), can also be used for transdermal delivery of the muteins described herein. Non-parenteral delivery modes are, for instance, oral, e.g. in the form of pills, tablets, capsules, solutions or suspensions, or rectal administration, e.g. in the form of suppositories. The muteins of present disclosure can be administered systemically or topically in formulations containing a variety of conventional non-toxic pharmaceutically acceptable excipients or carriers, additives, and vehicles.

The dosage of the mutein applied may vary within wide limits to achieve the desired preventive effect or therapeutic response. It will, for instance, depend on the affinity of the compound for a chosen ligand as well as on the half-life of the complex between the mutein and the ligand in vivo. Further, the optimal dosage will depend on the biodistribution of the mutein or its fusion protein or its conjugate, the mode of administration, the severity of the disease/disorder being treated as well as the medical condition of the patient. For example, when used in an ointment for topical applications, a high concentration of a protein of present disclosure can be used. However, if wanted, the protein may also be given in a sustained release formulation, for example liposomal dispersions or hydrogel-based polymer microspheres, like PolyActive™ or OctoDEX™ (cf. Bos et al., Business Briefing: Pharmatech 1-6 (2003)).

Accordingly, the muteins of the present disclosure can be formulated into compositions using pharmaceutically acceptable ingredients as well as established methods of preparation (see, e.g., Gennaro and Gennaro, Remington: The Science and Practice of Pharmacy, 20th Ed., Lippincott Williams & Wilkins, Philadelphia, Pa. (2000)). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

A mutein of the present disclosure or a fusion protein or a conjugate thereof can be employed in many applications. In general, such a mutein can be used in all applications antibodies are used, except those which specifically rely on the glycosylation of the Fc part.

A mutein described herein can be administered to an organism, including a human patient per se, or in a pharmaceutical composition where it may include or be mixed with pharmaceutically active ingredients or suitable carriers or excipient(s). Techniques for formulation and administration of a respective lipocalin mutein composition resemble or are identical to those of low molecular weight compounds well established in the art. Exemplary routes include, but are not limited to, oral, transdermal, and parenteral delivery. A lipocalin mutein or a respective composition may be used to fill a capsule or tube, or may be provided in compressed form as a pellet. The lipocalin mutein or a respective composition may also be used in injectable or sprayable form, for instance as a suspension of a respective lipocalin mutein.

A composition that includes a lipocalin mutein of present disclosure may for instance be applied onto the skin or onto a wound. Further suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. In some embodiments one may administer a lipocalin mutein or a respective composition in a local rather than systemic manner, for example, via injection.

Pharmaceutical compositions that include a lipocalin mutein of the present disclosure may be manufactured in a manner that is itself known, e.g., by means of conventional mixing, dissolving, granulating, dragee-making, levigating, emulsifying, encapsulating, entrapping or lyophilizing processes. A pharmaceutical composition for use in accordance with the present disclosure thus may be formulated in conventional manner using one or more physiologically acceptable carriers including excipients and auxiliaries that facilitate processing of the hydrogel and/or peptide/peptoid into preparations that can be used pharmaceutically. Proper formulation is dependent upon the route of administration chosen.

For injection, the lipocalin mutein or a respective composition may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the lipocalin mutein or a respective composition can be formulated readily by combining them with pharmaceutically acceptable carriers well known in the art. Such carriers enable the lipocalin mutein or a respective composition, as well as a pharmaceutically active compound where present, to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the peptides/peptoids may be suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in a conventional manner.

A lipocalin mutein of the present disclosure may be formulated for parenteral administration by injection, e.g., by intramuscular injections or bolus injection or continuous infusion. Formulations for injection may be presented in unit dosage form, e.g., in ampules or in multi-dose containers, with an added preservative. The respective compositions may take such forms as suspensions, solutions or emulsions in oily or aqueous vehicles, and may contain formulatory agents such as suspending, stabilizing and/or dispersing agents.

A lipocalin mutein of the present disclosure may also be used to target a compound to a pre-selected site. In one such embodiment, a lipocalin mutein of present disclosure is used for the targeting of a pharmaceutically active compound to a pre-selected site in an organism or tissue, comprising:
a) conjugating the lipocalin mutein with said compound, and
b) delivering the lipocalin mutein/compound complex to the pre-selected site.

For such a purpose the mutein is contacted with the compound of interest in order to allow complex formation. Then the complex comprising the mutein and the compound of interest are delivered to the pre-selected site. This may, for example, be achieved by coupling the mutein to a targeting moiety, such as an antibody, antibody fragment or lipocalin mutein or lipocalin mutein fragment with binding affinity for the selected target.

This use is in particular suitable, but not restricted to, for delivering a drug (selectively) to a pre-selected site in an organism, such as an infected body part, tissue or organ which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the pre-selected target site. Such a conjugate of mutein and compound may also include a linker that covalently links mutein and compound to each other. Optionally, such a linker is stable in the bloodstream but is cleavable in a cellular environment.

The muteins disclosed herein and their derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. For example, muteins of present disclosure can serve to detect chemical structures by means of established analytical methods (e.g., ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of present disclosure, which binds, for example, tissue- or tumor-specific cellular surface molecules can be generated. Such a mutein may, for example, be employed in conjugated form or as a fusion protein for "tumor imaging" or directly for cancer therapy.

In a further aspect, the present disclosure also encompasses the use of a mutein according to present disclosure for the manufacture of a pharmaceutical composition. The pharmaceutical composition thus obtained may be suited for the treatment of anaemia. The pharmaceutical composition may be used as monotherapy or as combination therapy. Accordingly, present disclosure also relates to a mutein as defined above for the treatment of a disease or disorder associated with an altered, e.g. increased or reduced, level of GPC3, such as anaemia.

In yet another aspect present disclosure relates to the use of a mutein according to present disclosure in diagnosis. The use of a mutein according to present disclosure is typically for the diagnosis of a disease or disorder associated with an altered level of GPC3 as well as a respective method of diagnosis.

Accordingly, the present disclosure also relates to a mutein as defined above for the diagnosis of a disease or disorder associated with an altered, for example increased or reduced, level of GPC3. In some embodiments the disease is cancer, including, but not limited to, liver cancer or melanoma. The cancer to be diagnosed is not particularly limited, and specific examples may include liver cancer, pancreatic cancer, cholangiocarcinoma, lung cancer, colon cancer, colorectal malignancies, neurofibrosarcoma, neuroblastoma, mammary cancer, breast cancer, ovarian cancer, prostate cancer, leukemia and lymphoma, Wilm's tumor, preferably liver cancer or (primary/early) hepatocellular carcinoma. (See Sinnett D., GPC3 (glypican 3), Atlas Genet Cytogenet Oncol Haematol. 2002; 6(3):206-208 (2002).)

Also, the present disclosure relates to a method of treating a tumor or cancer, the method comprising administering a pharmaceutical composition as described herein containing a mutein of the present disclosure to a subject in need thereof. Likewise, the present disclosure relates to a mutein of present disclosure for use in (a method of) treating a tumor or cancer. Similarly, present disclosure concerns the use of a mutein of present disclosure for the preparation of a pharmaceutical composition for treating a tumor or cancer. The cancer or tumor to be treated is not particularly limited, and specific examples may include liver cancer, pancreatic cancer, cholangiocarcinoma, lung cancer, colon cancer, colorectal malignancies, neurofibrosarcoma, neuroblastoma, mammary cancer, breast cancer, ovarian cancer, prostate cancer, leukemia and lymphoma, Wilm's tumor, preferably liver cancer or (primary/early) hepatocellular carcinoma. (See Sinnett D., GPC3 (glypican 3), Atlas Genet Cytogenet Oncol Haematol. 2002; 6(3):206-208 (2002).)

In still another aspect, the present disclosure features a diagnostic or analytical kit comprising a mutein according to the present disclosure.

The subject in need of such a treatment may be a mammal, such as a human, a dog, a mouse, a rat, a pig, an ape such as cynomolgous monkeys to name only a few illustrative examples.

In still another aspect, the present disclosure features a method for in vivo imaging in a subject, including administering to said subject a mutein of present disclosure or a pharmaceutical composition comprising a mutein of present disclosure. The subject may be defined as above.

The mutein of the disclosure may be conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, and colloidal gold.

The mutein of the disclosure may be fused at its N-terminus and/or its C-terminus to a fusion partner which is a protein, or a protein domain or a peptide.

The mutein of the disclosure may be conjugated to a compound that extends the serum half-life of the mutein. In some embodiments, the compound may extend the serum half-life is selected from the group consisting of a polyalkylene glycol molecule, hydroethylstarch, a Fc part of an immunoglubolin, a CH3 domain of an immuoglobulin, a CH4 domain of an immunoglubolin, an albumin binding peptide, and an albumin binding protein. In some further embodiments, the polyalkylene glycol is polyethylene (PEG) or an activated derivative thereof.

In some other embodiments, the fusion partner of the mutein is a protein domain that extends the serum half-life of the mutein.

In some additional embodiments, the protein domain is an Fc part of an immunoglobulin, a CH3 domain of an immunoglobulin, a CH4 domain of an immunoglobulin, an albumin binding peptide, or an albumin binding protein.

The mutein of the present disclosure may be for use in (a method of) therapy or diagnosis; such as for use in (a method of) treatment or (a method of) diagnosis of a tumor, preferably liver tumor; or for use in (a method of) inhibiting growth of tumor; or for use in (a method of) the treatment or diagnosis of liver tumor.

The present disclosure further provides a nucleic acid molecule comprising a nucleotide sequence encoding a mutein of the disclosure. In some embodiments, the nucleic acid molecule is operably linked to a regulatory sequence to allow expression of said nucleic acid molecule. In some still further embodiments, the nucleic acid molecule is comprised in a vector or in a phagemid vector.

The present disclosure also discloses a host cell containing a nucleic acid molecule of the disclosure.

Moreover, the present disclosure furnishes the skilled with a method of producing a mutein of the disclosure, wherein the mutein, a fragment of the mutein or a fusion protein of the mutein and another polypeptide is produced starting from the nucleic acid coding for the mutein by means of genetic engineering methods. In some further embodiments, the mutein is produced in a bacterial or eucaryotic host organism and is isolated from this host organism or its culture.

The present disclosure contemplates a pharmaceutical composition comprising a mutein of the disclosure and a pharmaceutically acceptable excipient.

The present disclosure illustrates the use of a mutein of the disclosure for the binding/detection of GPC3, comprising:
(a) contacting the mutein with a test sample suspected to contain GPC3, thereby allowing the formation of a complex between the mutein and GPC3, and
(b) detecting the complex between the mutein and GPC3 by a suitable signal.

The present disclosure reveals to the skilled a method of treating a tumor, the method comprising administering a mutein of the disclosure or a pharmaceutical composition thereof to a subject in need thereof. In some further embodiments, the tumor is liver cancer, (primary/early) hepatocellular carcinoma, pancreatic cancer, cholangiocarcinoma, lung cancer, colon cancer, colorectal malignancies, neurofibrosarcoma, neuroblastoma, mammary cancer, breast cancer, ovarian cancer, prostate cancer, leukemia and lymphoma, or Wilm's tumor.

The disclosure imparts a method of detecting the presence of GPC3 in a biological sample, comprising: contacting the sample with a mutein of the disclosure under conditions that allow the formation of a complex of the mutein and GPC3. In some embodiments, the method further comprises detecting the complex of the mutein and GPC3. In some further embodiments, the biological sample is isolated from a human. In some additional embodiments, the sample comprises body fluid.

The disclosure makes known a method of binding GPC3 in a subject comprising administering to said subject an effective amount of one or more muteins of the disclosure or of one or more compositions comprising such muteins.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of present disclosure described herein. Such equivalents are intended to be encompassed by the present disclosure.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, this specification will supersede any such material. Nothing herein is to be construed as an admission that present disclosure is not entitled to antedate such disclosure by virtue of prior invention.

Unless otherwise indicated, established methods of recombinant gene technology were used, for example, as described in Sambrook et al. (2001), supra.

Additional objects, advantages, and features of the present disclosure will become apparent to those skilled in the art upon examination of the following Examples and the attached FIGURES thereof, which are not intended to be limiting. Thus, it should be understood that although the present disclosure is specifically disclosed by exemplary embodiments and optional features, modification and variation of the disclosures embodied herein may be resorted to by those skilled in the art, and that such modifications and variations are considered to be within the scope of this disclosure.

IV. EXAMPLES

Example 1: Generation of Maturation Libraries and Selection of Optimized Muteins Specifically Binding to GPC3

For optimization of GPC3-specific muteins, libraries were generated based on mutein SEQ ID NOs: 3 and 4 using either a biased randomization of selected positions or error prone polymerase chain reaction (PCR) based methods. The biased design was made such that for each of the selected positions the amino acid encoded corresponds to the amino acid found in the respective mother clone with a probability of 50-70%, while it can be a different amino acid with a 50-30% probability. With N the number of targeted positions and B as bias, the most probable number of exchanges per clone is $N \times (1-B)$. In order to facilitate expression in eukaryotic cells, the hNGAL-derived natural N-glycosylation site N65 was removed by the mutation N65D; and as for other potential N-glycosylation sites (Asn-X-Ser/Thr), the likelyhood to occur was reduced by setting a bias at those library positions. The removal of SS-bridges in selected libraries was accomplished by setting a 50% bias with valine as main amino acid at position C76 and by the mutation of C175A.

Phage display was employed to select for optimized muteins with improved heat stability and binding affinity. The phagemid selection was conducted with increased stringency compared to the initial mutein selections and involved preincubation steps at elevated temperature and limiting target concentration amongst other things.

Example 2: Identification of Muteins with Improved Binding to GPC3 and Improved Heat Stability Using High-Throughput ELISA Screening Individual colonies were used to inoculate 2×YT/Amp medium and grown overnight (14-18 hours) to stationary phase. Subsequently, 50 µl 2×YT/Amp were inoculated from the stationary phase cultures and incubated for 3 hours at 37° C. and then shifted to 22° C. until an $OD_{595}$ of 0.6-0.8 was reached. Production of muteins was induced by addition of 10 µl 2×YT/Amp supplemented with 1.2 µg/ml anhydrotetracyclin. Cultures were incubated at 22° C. until the next day. After addition of 40 µl of 5% (w/v) BSA in PBS/T and incubation for 1 hour at 25° C. cultures were ready for use in screening assays. While 20 µl of the cultures were directly applied to the screening ELISA plate, the residual volume was incubated at 65° C. for 1 h.

Binding of the isolated muteins to GPC3 was tested by coating a 1:1 mixture of neutravidin and streptavidin (5 µg/ml in PBS) overnight at 4° C. on microtiter plates. After blocking the plate with 2% BSA in PBST biotinylated GPC3 was captured on the coated microtiter plates at a concentration of 1 µg/ml in PBS/T. Subsequently, 20 µl of BSA-blocked cultures (with or without previous heat incubation) were added to the microtiter plates and incubated for 1 hour at 25° C. Bound muteins were detected with anti-Streptag antibody conjugated with horseradish peroxidase (1-hour incubation; 2-1509-001; IBA). For quantification, 20 µl of QuantaBlu fluorogenic peroxidase substrate was added and the fluorescence was determined at an excitation wavelength of 330 nm and an emission wavelength of 420 nm.

In addition, reverse screening formats were applied, where the muteins were captured via the Streptag on microtiter plates coated with anti-Streptag antibody and different concentrations of biotinylated target were added and detected via Extravidin-HRP (E2886; Sigma).

Clones were then sequenced based on the screening results and muteins were selected for further characterization. After the selection of optimized lipocalin muteins, a His 28→Gln mutation was introduced to further optimize stability.

Example 3: Expression of Muteins

Unique muteins were expressed with C-terminal sequence SAWSHPQFEK (SEQ ID NO: 17); including the SA linker and the Strep-tag® II, WSHPQFEK (SEQ ID NO: 18) in *E. coli* in 2YT-Amp medium to purify the muteins after expression using Streptactin affinity chromatography and preparative size exclusion chromatography.

Example 4: Measurement of Binding Affinity for Human and Murine GPC3 Via Surface Plasmon Resonance Surface plasmon resonance (SPR) was used to measure binding kinetics and affinity of the optimized lipocalin muteins disclosed herein.

SPR analysis of the binding of the optimized Lcn2 muteins to human and mouse GPC3 was performed at 25° C. on a Biacore T200 instrument (GE Healthcare) using HBS-EP+ (1×; BR-1006-69; GE Healthcare) as running buffer. The Biotin CAPture Kit (GE Healthcare) was used to immobilize biotinylated GPC3 to a chip surface. Human GPC3 (2119-GP; R&D systems) and murine GPC3 (6938-GP; R&D systems) were biotinylated using standard NHS chemistry. Undiluted Biotin CAPture Reagent (streptavidin conjugated with ss-DNA oligo) was captured on a Sensor Chip CAP with the pre-immobilized complementary ss-DNA oligo. Thereafter, biotinylated human or murine GPC3 at 1 µg/ml was applied for 300 s at a flow rate of 5 µg/mL.

Lcn2 muteins were applied in concentrations of 10 nM, 40 nM and 160 nM at a flow rate of 30 µL/min. The dilutions were injected with association times of 180 s and dissociation times of 600 s to obtain ka and kd information. Regeneration of the chip surface was achieved by injecting 6 M Guanidinium-HCl+0.25 M NaOH (120 s) with a flow rate of 10 µL/min. Injection of regeneration solutions was followed by an extra wash step with $H_2O$ and a stabilization period of 120 s.

The data were double-referenced by subtraction of the corresponding signals measured for the control channel (loaded with Biotin CAPture reagent only) and by subtraction of buffer injections from the binding responses. Association rate constant ka and dissociation rate constant kd for the binding reaction were determined using Biacore T200 Evaluation Software V2.0 for data processing and kinetic fitting. The data were globally fit with 1:1 binding model.

The values determined for ka, kd and the resulting equilibrium dissociation constant ($K_D$) for SEQ ID NOs: 3 and 4 and the optimized muteins of SEQ ID NOs: 5 to 16 are summarized in Table 1. Optimized GPC3 specific lipocalin muteins bind human as well as murine GPC3 with picomolar to low nanomolar affinity and affinities are up to 30-fold improved after optimization.

TABLE 1

Affinities, association rate constants ka and dissociation rate constants kd of optimized muteins for human and murine GPC3 as determined by surface-plasmon-resonance (SPR).

| | human GPC3 | | | mouse GPC3 | | |
|---|---|---|---|---|---|---|
| SEQ ID NO: | ka [$M^{-1} \cdot s^{-1}$] | kd [$s^{-1}$] | $K_D$ [nM] | ka [$M^{-1} \cdot s^{-1}$] | kd [$s^{-1}$] | $K_D$ [nM] |
| 3 | 5.6E+05 | 2.2E−04 | 0.387 | 4.5E+05 | 3.0E−04 | 0.674 |
| 7 | 1.3E+06 | 1.3E−04 | 0.097 | 1.0E+06 | 1.5E−04 | 0.145 |
| 5 | 1.6E+06 | 2.0E−04 | 0.119 | 1.3E+06 | 2.6E−04 | 0.207 |
| 6 | 1.8E+06 | 3.3E−05 | 0.019 | 2.2E+06 | 4.2E−05 | 0.019 |
| 4 | 2.5E+06 | 2.2E−03 | 0.877 | 2.6E+06 | 2.8E−03 | 1.091 |

TABLE 1-continued

Affinities, association rate constants ka and dissociation rate
constants kd of optimized muteins for human and murine GPC3 as
determined by surface-plasmon-resonance (SPR).

| | human GPC3 | | | mouse GPC3 | | |
|---|---|---|---|---|---|---|
| SEQ ID NO: | ka [$M^{-1} \cdot s^{-1}$] | kd [$s^{-1}$] | $K_D$ [nM] | ka [$M^{-1} \cdot s^{-1}$] | kd [$s^{-1}$] | $K_D$ [nM] |
| 13 | 2.6E+06 | 1.8E−04 | 0.070 | 2.7E+06 | 2.4E−04 | 0.090 |
| 9 | 1.8E+06 | 9.8E−05 | 0.054 | 2.0E+06 | 1.5E−04 | 0.075 |
| 8 | 2.0E+06 | 1.3E−04 | 0.068 | 1.9E+06 | 1.8E−04 | 0.096 |
| 10 | 1.8E+06 | 1.2E−04 | 0.063 | 1.8E+06 | 1.7E−04 | 0.093 |
| 12 | 6.5E+06 | 2.4E−04 | 0.037 | 5.1E+06 | 3.0E−04 | 0.058 |
| 11 | 1.7E+06 | 4.6E−05 | 0.027 | 2.9E+06 | 3.2E−05 | 0.011 |
| 14 | 2.4E+06 | 2.0E−03 | 0.819 | 2.0E+06 | 3.1E−03 | 1.594 |
| 15 | 1.4E+06 | 4.9E−05 | 0.035 | 1.3E+06 | 9.1E−05 | 0.072 |
| 16 | 6.7E+05 | 1.1E−04 | 0.171 | 6.1E+05 | 1.9E−04 | 0.311 |

Example 5: Binding of Optimized Lipocalin Muteins to Human, Cynomolgus and Mouse GPC3 Transfected SK-HEP-1 Cells SK-HEP-1 cells from the DSMZ cell bank that do not express detectable levels of endogenous GPC3 as assessed by flow cytometry were stably transfected with an expression vector encoding human, cynomolgus or mouse GPC3. Empty vector control cells were also obtained and analyzed in parallel.

Binding of optimized lipocalin muteins of SEQ ID NOs: 5-16 to human, cynomolgus and mouse GPC3 compared to SEQ ID NOs: 3 and 4 was tested on SK-HEP-1 cells using an ECL format (FIG. 1). In this experiment, dilution series of lipocalin muteins were incubated on MSD plates coated with human, cynomolgus or mouse GPC3 overexpressing SK-HEP-1 cells.

All incubation steps were performed at room temperature and the plates were washed after each incubation step with 80 μL PBS buffer for two times using a Biotek EL405 select CW washer.

In the first step, a 384 well plate was precoated for 5 minutes with poly-D-lysine and washed twice with PBS. 10 000 SK-HEP-1 cells per well were seeded and allowed to adhere overnight at 37° C. After washing, cell coated wells were blocked with 60 μl PBS/Casein (0.1% Casein in PBS).

SEQ ID NOs: 3, 4, 5, 7, 8, 9, 10, 12, 13, 14, 15 and 16 (using 1000 nM as starting concentration) were serially diluted at a 1:3 ratio down to the picomolar range in PBS/Casein. 20 μl of the dilution series were transferred to the SK-HEP-1-coated plates for 1 hour at room temperature.

To allow for detection and quantification of bound GPC3 specific lipocalin muteins, the residual supernatants were discarded and 20 μl of a mixture of rabbit anti scaffold antibody (2 μg/ml) and Sulfotag labelled anti rabbit antibody (5 μg/ml) prepared in PBS/casein was added to the wells and incubated for 1 h at RT. After washing, 35 μl surfactant-free reading buffer was added to each well and the ECL intensity of every well was read using a MSD reader.

Curve fitting was performed using GraphPad Prism 4 software.

Most of the optimized GPC3 specific Lcn2 muteins bind SK-HEP-1 cells transfected with human, mouse or cynomolgus GPC3 with improved EC50 values compared to SEQ ID NOs: 3 and 4. Exemplary binding curves are shown in FIG. 1 and EC50 values for binding to SK-HEP-1::human GPC3, SK-HEP-1::mouse GPC3 and SK-HEP-1::cynomolugus GPC3 are summarized in Table 2.

TABLE 2

EC50 values for binding of optimized lipocalin muteins
compared to SEQ ID NOs: 3 and 4 to immobilized SK-HEP-1 cells
transfected with human, murine or cynomolgus GPC3, respectively as
obtained in an MSD-based cell binding assay. The majority of optimized
muteins exhibits lower EC50 values compared to SEQ ID NOs: 3 and 4
indicating improved binding to GPC3 expressed on cells. All
muteins show crossreactivity with murine and cynomolgus GPC3.

| SEQ ID NO: | EC50 [nM] SK-HEP-1:: human GPC3 | EC50 [nM] SK-HEP-1:: mouse GPC3 | EC50 [nM] SK-HEP-1:: cyno GPC3 |
|---|---|---|---|
| 3 | 24.3 | 29.8 | 29.9 |
| 7 | 2.5 | 4.8 | 2.8 |
| 5 | 24.1 | 25.6 | 33.9 |
| 4 | 10.2 | 7.1 | 5.7 |
| 13 | 0.9 | 2.9 | 0.6 |
| 9 | 1.1 | 4.1 | 1.9 |
| 8 | 1.4 | 5.3 | 2.3 |
| 10 | 0.8 | 3.8 | 0.8 |
| 12 | 2.0 | 5.3 | 1.7 |
| 14 | 9.5 | 6.7 | 15.4 |
| 15 | 1.6 | 4.8 | 1.6 |
| 16 | 2.2 | 4.4 | 2.5 |

Example 6: Measurement of Thermal Stability Via a Fluorescence-Based Thermal Denaturation Assay A fluorescence-based thermal denaturation assay (commonly referred to as thermal shift assay of differential scanning fluorometry) was employed to measure the thermal stability of human GPC3-specific Lcn2 muteins using Mx3005P qPCR System (Agilent Technologies).

Lipocalin mutein solutions were diluted to a concentration of 10 μM in phosphate-buffered saline (PBS; pH 7.4; 10010; Life Technologies) and a 15-fold stock solution in PBS of the fluorescent dye SYPRO Orange (5000× concentrate in DMSO; S-6650; Life technologies) was prepared. 20 μl of protein dilution was mixed with 5 μl of SYPRO Orange stock in a qPCR plate (FrameStar 96 non skirted; Cat No 4ti-0711; 4titude) and the plate was sealed with caps (Flat Optically Clear Caps; Cat No 4Ti-0751; 4titude). Using an Mx3005P qPCR System the plate was gradually heated from 25° C. to 100° C. (45 s/step) while the fluorescence signal was recorded at an excitation wavelength of 492 nm and an emission wavelength of 610 nm.

An increase in fluorescence indicates protein unfolding, as SYPRO Orange binds nonspecifically to hydrophobic surfaces and water strongly quenches the fluorescence of Sypro Orange. (See Kranz J. and Schalk-Hihi, C., Protein thermal shifts to identify low molecular weight fragments, Methods Enzymol. 493: 277-298 (2011).).

Savitzky-golay smoothing (5× savitzky golay filter) was applied to the raw data (fluorescence signal over temperature) and the first derivative was calculated. For determination of the melting temperature $^{TM}$, the maximum of the first derivative (corresponding to the inflection point of the fluorescence-over-temperature curve) was read out and matched with the corresponding temperature (=Tm). The complete evaluation was performed in Microsoft Excel.

The melting temperatures (Tm) of the lipocalin muteins as determined in the thermal shift assay described above are compiled in Table 3.

TABLE 3

Melting temperatures (Tm) of optimized lipocalin muteins specific for GPC3 as determined by a thermal shift assay using SYPRO Orange dye. For the optimized lipocalin muteins the increase in melting temperature is up to 14° C. compared to the non-optimized muteins.

| SEQ ID NO: | Tm [° C.] |
|---|---|
| 3 | 58 |
| 7 | 67 |
| 5 | 65 |
| 6 | 65 |
| 4 | 55 |
| 13 | 68 |
| 9 | 68 |
| 8 | 68 |
| 10 | 69 |
| 12 | 64 |
| 11 | 58 |
| 14 | 61 |
| 15 | 52 |
| 16 | 53 |

Example 7: Assessment of Storage Stability in Buffer and Plasma of Selected Optimized GPC3 Specific Lipocalin Muteins To assess storage stability of exemplary selected muteins (SEQ ID NOs: 7, 9 and 10) in non-optimized formulation (PBS pH 7.4) and human and murine plasma the following stability studies were conducted:

For investigation of storage stability in buffer muteins were diluted to a concentration of 1 mg/ml in PBS (phosphate-buffered saline pH 7.4; 10010; Life Technologies) and one aliquot was incubated for 1 week at 42° C., while a reference aliquot was frozen at −20° C. Active mutein was measured in a quantitative ELISA setting. Monomeric protein was measured in an analytical size exclusion chromatography.

To assess stability in plasma samples mutein dilutions in 50% human or murine plasma in PBS at a concentration of 0.5 mg/ml were prepared and incubated at 37° C. for 1 week (a reference aliquot of the preparation was immediately frozen at −20° C.). Active mutein concentration was evaluated by a qELISA.

For assaying protein activity, the following ELISA was applied: A 384-well polystyrene plate (Greiner FLUOTRAC™ 600; black flat bottom; high-binding) was coated with 20 μL of GPC3 (2119-GP; R&D Systems) at a concentration of 5 μg/ml in PBS overnight at 4° C. After washing, wells were blocked with 100 μl blocking buffer (2% w/v BSA in PBS containing 0.1% v/v Tween-20). The plate was washed and 20 μl of appropriately diluted protein standard, of unstressed reference sample (stored at −20° C. after preparation) or of stressed sample was transferred to the ELISA plate and incubated. To detect plate-bound protein, the ELISA plate was washed, residual supernatants were discarded and 20 μl HRP-labeled anti-hNGAL antibody was added at a predetermined optimal concentration in blocking buffer and incubated. After washing, 20 μl of fluorogenic HRP substrate (QuantaBlu; Pierce) was added to each well and the reaction was allowed to proceed for 5 minutes. The fluorescence intensity of every well on the plate was read using a fluorescence microplate reader (Tecan).

Unless otherwise stated, all incubation steps were performed for 1 hour at room temperature and after each incubation step the plate was washed with 100 μl PBS-T buffer (PBS; 0.05% Tween 20) for five times using a Biotek ELx405 select CW washer.

For the ELISA described above, a calibration curve including 11 mutein dilutions typically ranging from 0.01-1000 ng/mL was prepared and three different, independent dilutions within the linear range of the calibration curve were prepared for each sample. Blocking buffer optionally supplemented with 1% human or murine plasma was used for the dilutions.

The calibration curve was fit using a 4 Parameter Logistic (4PL) nonlinear regression model and used to calculate active protein concentrations for the tested samples. The determined active protein concentrations were referenced against an unstressed reference sample stored at −20° C. at the same concentration and in the same matrix.

Analytical size exclusion chromatography was performed on an Agilent HPLC system with two Superdex 75 5/150 GL columns (GE Healthcare) in a row using PBS (10010; Life Technologies) as an eluent at a flow rate of 0.3 mL/min.

The results of the storage stability testing in PBS pH 7.4 and human and murine plasma are summarized in Table 4.

TABLE 4

Storage stability in non-optimized formulation (PBS; 1 week; 42° C.), human and murine plasma (1 week; 37° C.) assessed by recovery of activity in qELISA and monomer content in analytical SEC: stable in qELISA = 100 +/− 15% (recovery of mutein activity compared to non-stressed reference sample); stable in aSEC = 100 +/− 5% (recovery of monomer peak area compared to non-stressed reference sample); For all samples including references a monomer content of 100 area percent was detected.

| SEQ ID NO: | Human plasma: 1 week at 37° C. recovery of mutein activity [%] | Mouse plasma: 1 week at 37° C. recovery of mutein activity [%]] | PBS: 1 week at 42° C. recovery of mutein activity [%] | PBS: 1 week at 42° C. recovery of monomer peak area [%] |
|---|---|---|---|---|
| 7 | 98 | 105 | 93 | 103 |
| 9 | 92 | 101 | 96 | 105 |
| 10 | 105 | 95 | 101 | 98 |

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

EQUIVALENTS

Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

The invention claimed is:

1. A nucleic acid molecule comprising a nucleotide sequence encoding a human neutrophil gelatinase-associated lipocalin (hNGAL) mutein capable of binding glypican-3 (GPC3) with detectable affinity, wherein the mutein comprises a mutated amino acid residue at the sequence position 65 in comparison with the linear polypeptide sequence of mature hNGAL (SEQ ID NO: 1), wherein the mutein comprises at least eight of the following mutated amino acid residues in comparison with the linear polypeptide sequence of mature hNGAL (SEQ ID NO: 1): Leu 36→Val or Arg; Ala 40→Leu, Val or Gly; Ile 41→Leu, Arg, Met, Gly or Ala; Gln 49→Pro or Leu; Tyr 52 Arg or Trp; Asn 65→Asp; Ser 68→Val, Gly, Asn or Ala; Leu 70→Ser, Ala or Val; Arg 72→Asp, Trp, Ala, or Gly; Lys 73→Gly, Arg, Asn, Glu or Ser; Cys 76→Val or Ile; Asp 77→His, Met, Val, Leu, Thr or Lys; Trp 79→Lys, Ser or Thr; Arg 81→Gly; Cys 87→Ser; Asn 96→Arg, Asp, Gln or Pro; Tyr 100→Gly, Glu, Pro or Gln; Leu 103→Glu, Gln, Asn, Gly, Ser, Asp, or Tyr; Ser 105→Ala; Tyr 106→Asn, Ser or Thr; Lys 125→Glu; Ser 127→Arg or Tyr; Tyr 132→Trp or Ile; Lys 134→Ala or Phe; Thr 136→Ile; and Cys 175→Ala, and wherein the mutein has at least 85% sequence identity to an amino acid sequence selected from the group consisting of SEQ ID NOs: 5-16.

2. The nucleic acid molecule of claim 1, wherein the mutein comprises the following mutated amino acid residue in comparison with the linear polypeptide sequence of mature hNGAL (SEQ ID NO: 1): Asn 65→Asp.

3. The nucleic acid molecule of claim 1, wherein the mutein binds human GPC3 with a $K_D$ of about 0.3 nM or lower.

4. The nucleic acid molecule of claim 1, wherein the mutein binds GPC3 with a stronger binding affinity than the mutein of SEQ ID NO: 3.

5. The nucleic acid molecule of claim 1, wherein the mutein exhibits a lower $EC_{50}$ value compared to the mutein of SEQ ID NO: 4 when binding to human, mouse or cynomolgus GPC3 expressed on HEP-1 cells.

6. The nucleic acid molecule of claim 1, wherein the mutein has improved thermal stability compared to the mutein of SEQ ID NO: 3.

7. The nucleic acid molecule of claim 1, wherein the mutein comprises one of the following sets of mutated amino acid residues in comparison with the linear polypeptide sequence of mature hNGAL (SEQ ID NO: 1):

(a) Leu 36→Val; Ile 41→Leu; Gln 49→Leu; Tyr 52 Arg; Asn 65→Asp; Ser 68→Val; Leu 70→Ser; Arg 72→Trp; Lys 73→Arg; Asp 77→His; Trp 79→Lys; Arg 81→Gly; Cys 87→Ser; Asn 96→Asp; Tyr 100→Gly; Leu 103→Gln; Tyr 106→Asn; Lys 125→Glu; Ser 127→Arg; Tyr 132→Trp; and Lys 134→Ala;

(b) Leu 36→Val; Ala 40→Val; Ile 41→Arg; Gln 49→Pro; Tyr 52 Arg; Asn 65→Asp; Ser 68→Gly; Leu 70→Ser; Lys 73→Gly; Asp 77→His; Trp 79→Lys; Arg 81→Gly; Cys 87→Ser; Asn 96→Asp; Tyr 100→Gly; Leu 103→Glu; Tyr 106→Asn; Lys 125→Glu; Ser 127→Arg; Tyr 132→Trp; and Lys 134→Phe;

(c) Leu 36→Val; Ala 40→Gly; Ile 41→Met; Gln 49→Leu; Tyr 52 Arg; Asn 65→Asp; Leu 70→Ala; Lys 73→Asn; Asp 77→His; Trp 79→Lys; Arg 81→Gly; Cys 87→Ser; Asn 96→Gln; Tyr 100→Gly; Leu 103→Glu; Tyr 106→Asn; Lys 125→Glu; Ser 127→Arg; Tyr 132→Trp; and Lys 134→Phe;

(d) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Arg; Asp 77→Leu; Trp 79→Ser; Arg 81→Gly; Cys 87→Ser; Asn 96→Gln; Tyr 100→Glu; Leu 103→Asn; Ser 105→Ala; Tyr 106→Asn; Lys 125→Glu; Ser 127→Tyr; Tyr 132→Ile; Lys 134→Phe; and Thr 136→Ile;

(e) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Arg; Asp 77→Thr; Trp 79→Ser; Arg 81→Gly; Cys 87→Ser; Asn 96→Gln; Tyr 100→Glu; Leu 103→Gly; Ser 105→Ala; Tyr 106→Asn; Lys 125→Glu; Ser 127→Tyr; Tyr 132→Ile; Lys 134→Phe; and Thr 136→Ile;

(f) Leu 36→Arg; Ala 40→Gly; Ile 41→Ala; Gln 49→Pro; Tyr 52→Trp; Asn 65→Asp; Ser 68→Asn; Leu 70→Arg; Arg 72→Ala; Lys 73→Arg; Asp 77→Val; Trp 79→Ser; Arg 81→Gly; Cys 87→Ser; Asn 96→Pro; Tyr 100→Glu; Leu 103→Asn; Ser 105→Ala; Tyr 106→Ser; Lys 125→Glu; Ser 127→Tyr; Tyr 132→Ile; Lys 134→Phe; and Thr 136→Ile;

(g) Leu 36→Arg; Ala 40→Val; Ile 41→Ala; Gln 49→Pro; Tyr 52→Arg; Asn 65→Asp; Ser 68→Ala; Leu 70→Arg; Arg 72→Ala; Lys 73→Arg; Asp 77→Leu; Trp 79→Ser; Arg 81→Gly; Cys 87→Ser; Asn 96→Arg; Tyr 100→Glu; Leu 103→Tyr; Ser 105→Ala; Tyr 106→Asn; Lys 125→Glu; Ser 127→Tyr; Tyr 132→Ile; Lys 134→Phe; and Thr 136→Ile;

(h) Leu 36→Arg; Ala 40→Val; Ile 41→Ala; Gln 49→Pro; Tyr 52→Arg; Asn 65→Asp; Ser 68→Asn; Leu 70→Val; Arg 72→Ala; Lys 73→Gly; Asp 77→Lys; Trp 79→Ser; Arg 81→Gly; Cys 87→Ser; Asn 96→Arg; Tyr 100→Pro; Leu 103→Asn; Ser 105→Ala; Tyr 106→Asn; Lys 125→Glu; Ser 127→Tyr; Tyr 132→Ile; Lys 134→Phe; and Thr 136→Ile;

(i) Leu 36→Arg; Ala 40→Leu; Ile 41→Gly; Gln 49→Pro; Tyr 52→Trp; Asn 65→Asp; Ser 68→Asn; Leu 70→Arg; Arg 72→Ala; Lys 73→Arg; Asp 77→Met; Trp 79→Ser; Arg 81→Gly; Cys 87→Ser; Asn 96→Gln; Tyr 100→Glu; Leu 103→Ser; Ser 105→Ala; Tyr 106→Asn; Lys 125→Glu; Ser 127→Tyr; Tyr 132→Ile; and Lys 134→Phe;

(j) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Gly; Cys 76→Val;

Asp 77→Lys; Trp 79→Thr; Arg 81→Gly; Cys 87→Ser; Asn 96→Gln; Tyr 100→Glu; Leu 103→Asn; Ser 105→Ala; Tyr 106→Thr; Lys 125→Glu; Ser 127→Tyr; Tyr 132→Ile; Lys 134→Phe; and Cys 175→Ala;

(k) Leu 36→Arg; Ala 40→Val; Ile 41→Gly; Gln 49→Pro; Tyr 52→Arg; Asn 65→Asp; Ser 68→Gly; Leu 70→Arg; Arg 72→Gly; Lys 73→Glu; Cys 76→Ile; Asp 77→Lys; Trp 79→Ser; Arg 81→Gly; Cys 87→Ser; Asn 96→Gln; Tyr 100→Gln; Leu 103→Asp; Ser 105→Ala; Tyr 106→Thr; Lys 125→Glu; Ser 127→Tyr; Tyr 132→Ile; Lys 134→Phe; Thr 136→Ile; and Cys 175→Ala; or (l) Leu 36→Arg; Ala 40→Val; Ile 41→Gly; Gln 49→Pro; Tyr 52→Arg; Asn 65→Asp; Ser 68→Gly; Leu 70→Arg; Arg 72→Asp; Lys 73→Ser; Cys 76→Val; Asp 77→Thr; Trp 79→Ser; Arg 81→Gly; Cys 87→Ser; Asn 96→Gln; Tyr 100→Glu; Leu 103→Asn; Ser 105→Ala; Tyr 106→Thr; Lys 125→Glu; Ser 127→Tyr; Tyr 132→Ile; Lys 134→Phe; Thr 136→Ile; Cys 175→Ala.

8. The nucleic acid molecule of claim 1, wherein the mutein has an amino acid sequence selected from the group consisting of SEQ ID NOs: 5-16.

9. The nucleic acid molecule of claim 1, wherein the mutein has at least 95% sequence identity to an amino acid sequence selected from the group consisting of SEQ ID NOs: 5-16.

10. A cell containing a nucleic acid molecule of claim 1.

11. A method of producing a mutein of claim 1, wherein the mutein is produced starting from the nucleic acid coding for the mutein.

\* \* \* \* \*

SEQUENCE LISTING

<160> NUMBER OF SEQ ID NOS: 30

<210> SEQ ID NO 1
<211> LENGTH: 178
<212> TYPE: PRT
<213> ORGANISM: artificial
<220> FEATURE:
<223> OTHER INFORMATION: Wildtype NGAL

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 2
<211> LENGTH: 178
<212> TYPE: PRT
<213> ORGANISM: artificial
<220> FEATURE:
<223> OTHER INFORMATION: Wildtype NGAL98

<400> SEQUENCE: 2

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 3
<211> LENGTH: 178
<212> TYPE: PRT
<213> ORGANISM: artificial
<220> FEATURE:
<223> OTHER INFORMATION: Lipocalin mutein - parental NGAL (P019-Seq2 -
      S375.1 M1.1 A16)

<400> SEQUENCE: 3

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Ala Met Leu Arg Glu Asp Lys Asp Pro
        35                  40                  45

Leu Lys Met Arg Ala Thr Ile Tyr Glu Leu Lys Glu Asp Lys Ser Tyr
    50                  55                  60

Asn Val Thr Gly Val Ser Phe Trp Arg Lys Lys Cys His Tyr Lys Ile
65                  70                  75                  80

Gly Thr Phe Val Pro Gly Ser Gln Pro Gly Glu Phe Thr Leu Gly Asp
                85                  90                  95

Ile Lys Ser Gly Pro Gly Gln Thr Ser Asn Leu Val Arg Val Val Ser
            100                 105                 110

Thr Asn Tyr Asn Gln His Ala Met Val Phe Phe Lys Glu Val Arg Gln
        115                 120                 125

Asn Arg Glu Trp Phe Ala Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160
```

Leu Pro Glu Asn His Ile Val Phe Pro Val Pro Ile Asp Gln Cys Ile
            165                 170                 175

Asp Gly

<210> SEQ ID NO 4
<211> LENGTH: 178
<212> TYPE: PRT
<213> ORGANISM: artificial
<220> FEATURE:
<223> OTHER INFORMATION: Lipocalin mutein - parental NGAL (P019-Seq 3 -
    S375.2 M1.1 M2)

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Val Ala Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asn Val Thr Asn Val Arg Phe Ala Met Lys Lys Cys Met Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Asn Thr Ser Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 5
<211> LENGTH: 178
<212> TYPE: PRT
<213> ORGANISM: artificial
<220> FEATURE:
<223> OTHER INFORMATION: Lipocalin mutein (S0569.05N06M1)

<400> SEQUENCE: 5

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Ala Leu Leu Arg Glu Asp Lys Asp Pro
        35                  40                  45

Leu Lys Met Arg Ala Thr Ile Tyr Glu Leu Lys Glu Asp Lys Ser Tyr
    50                  55                  60

Asp Val Thr Val Val Ser Phe Trp Arg Lys Lys Cys His Tyr Lys Ile
65                  70                  75                  80

Gly Thr Phe Val Pro Gly Ser Gln Pro Gly Glu Phe Thr Leu Gly Asp
                85                  90                  95

Ile Lys Ser Gly Pro Gly Gln Thr Ser Asn Leu Val Arg Val Val Ser
            100                 105                 110

Thr Asn Tyr Asn Gln His Ala Met Val Phe Phe Lys Glu Val Arg Gln
            115                 120                 125

Asn Arg Glu Trp Phe Ala Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 178
<212> TYPE: PRT
<213> ORGANISM: artificial
<220> FEATURE:
<223> OTHER INFORMATION: Lipocalin mutein (S0569.05K19M1)

<400> SEQUENCE: 6

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Val Arg Leu Arg Glu Lys Asp Pro
        35                  40                  45

Pro Lys Met Arg Ala Thr Ile Tyr Glu Leu Lys Glu Asp Lys Ser Tyr
    50                  55                  60

Asp Val Thr Gly Val Ser Phe Arg Gly Lys Lys Cys His Tyr Lys Ile
65                  70                  75                  80

Gly Thr Phe Val Pro Gly Ser Gln Pro Gly Glu Phe Thr Leu Gly Asp
                85                  90                  95

Ile Lys Ser Gly Pro Gly Glu Thr Ser Asn Leu Val Arg Val Val Ser
            100                 105                 110

Thr Asn Tyr Asn Gln His Ala Met Val Phe Phe Lys Glu Val Arg Gln
            115                 120                 125

Asn Arg Glu Trp Phe Phe Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 7
<211> LENGTH: 178
<212> TYPE: PRT
<213> ORGANISM: artificial
<220> FEATURE:
<223> OTHER INFORMATION: Lipocalin mutein (S0569.05O04M1)

<400> SEQUENCE: 7

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Gly Met Leu Arg Glu Asp Lys Asp Pro

```
            35                  40                  45
Leu Lys Met Arg Ala Thr Ile Tyr Glu Leu Lys Glu Asp Lys Ser Tyr
         50                  55                  60

Asp Val Thr Ser Val Ala Phe Arg Asn Lys Lys Cys His Tyr Lys Ile
 65                  70                  75                  80

Gly Thr Phe Val Pro Gly Ser Gln Pro Gly Phe Thr Leu Gly Gln
                 85                  90                  95

Ile Lys Ser Gly Pro Gly Glu Thr Ser Asn Leu Val Arg Val Val Ser
            100                 105                 110

Thr Asn Tyr Asn Gln His Ala Met Val Phe Phe Lys Glu Val Arg Gln
            115                 120                 125

Asn Arg Glu Trp Phe Phe Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 8
<211> LENGTH: 178
<212> TYPE: PRT
<213> ORGANISM: artificial
<220> FEATURE:
<223> OTHER INFORMATION: Lipocalin mutein (S0569.02J22M1)

<400> SEQUENCE: 8

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Arg Ala Gly Asn Val Gly Leu Arg Glu Asp Lys Asp Pro
            35                  40                  45

Pro Lys Met Trp Ala Thr Ile Tyr Glu Leu Lys Glu Asp Lys Ser Tyr
 50                  55                  60

Asp Val Thr Asn Val Arg Phe Ala Arg Lys Lys Cys Leu Tyr Ser Ile
 65                  70                  75                  80

Gly Thr Phe Val Pro Gly Ser Gln Pro Gly Glu Phe Thr Leu Gly Gln
                 85                  90                  95

Ile Lys Ser Glu Pro Gly Asn Thr Ala Asn Leu Val Arg Val Val Ser
            100                 105                 110

Thr Asn Tyr Asn Gln His Ala Met Val Phe Phe Lys Glu Val Tyr Gln
            115                 120                 125

Asn Arg Glu Ile Phe Phe Ile Ile Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 9
<211> LENGTH: 178
<212> TYPE: PRT
<213> ORGANISM: artificial
<220> FEATURE:

<223> OTHER INFORMATION: Lipocalin mutein (S0569.02B06M1)

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Gly Leu Arg Glu Asp Lys Asp Pro
        35                  40                  45

Pro Lys Met Trp Ala Thr Ile Tyr Glu Leu Lys Glu Asp Lys Ser Tyr
    50                  55                  60

Asp Val Thr Asn Val Arg Phe Ala Arg Lys Lys Cys Thr Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Gly Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 10
<211> LENGTH: 178
<212> TYPE: PRT
<213> ORGANISM: artificial
<220> FEATURE:
<223> OTHER INFORMATION: Lipocalin mutein (S0569.02L21M1)

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Gly Ala Leu Arg Glu Asp Lys Asp Pro
        35                  40                  45

Pro Lys Met Trp Ala Thr Ile Tyr Glu Leu Lys Glu Asp Lys Ser Tyr
    50                  55                  60

Asp Val Thr Asn Val Arg Phe Ala Arg Lys Lys Cys Val Tyr Ser Ile
65                  70                  75                  80

Gly Thr Phe Val Pro Gly Ser Gln Pro Gly Glu Phe Thr Leu Gly Pro
                85                  90                  95

Ile Lys Ser Glu Pro Gly Asn Thr Ala Ser Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 11
<211> LENGTH: 178
<212> TYPE: PRT
<213> ORGANISM: artificial
<220> FEATURE:
<223> OTHER INFORMATION: Lipocalin mutein (S0569.02A11M1)

<400> SEQUENCE: 11

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Ala Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asp Val Thr Ala Val Arg Phe Ala Arg Lys Lys Cys Leu Tyr Ser Ile
65                  70                  75                  80

Gly Thr Phe Val Pro Gly Ser Gln Pro Gly Glu Phe Thr Leu Gly Arg
                85                  90                  95

Ile Lys Ser Glu Pro Gly Tyr Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 12
<211> LENGTH: 178
<212> TYPE: PRT
<213> ORGANISM: artificial
<220> FEATURE:
<223> OTHER INFORMATION: Lipocalin mutein (S0569.09P24M1)

<400> SEQUENCE: 12

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Ala Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asp Val Thr Asn Val Val Phe Ala Gly Lys Lys Cys Lys Tyr Ser Ile
65                  70                  75                  80

Gly Thr Phe Val Pro Gly Ser Gln Pro Gly Glu Phe Thr Leu Gly Arg
                85                  90                  95

Ile Lys Ser Pro Pro Gly Asn Thr Ala Asn Leu Val Arg Val Val Ser

```
                  100                 105                 110
Thr Asn Tyr Asn Gln His Ala Met Val Phe Phe Lys Glu Val Tyr Gln
            115                 120                 125

Asn Arg Glu Ile Phe Phe Ile Ile Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 13
<211> LENGTH: 178
<212> TYPE: PRT
<213> ORGANISM: artificial
<220> FEATURE:
<223> OTHER INFORMATION: Lipocalin mutein (S0569.02N03M1)

<400> SEQUENCE: 13

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Leu Gly Leu Arg Glu Asp Lys Asp Pro
        35                  40                  45

Pro Lys Met Trp Ala Thr Ile Tyr Glu Leu Lys Glu Asp Lys Ser Tyr
    50                  55                  60

Asp Val Thr Asn Val Arg Phe Ala Arg Lys Lys Cys Met Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Ser Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 14
<211> LENGTH: 178
<212> TYPE: PRT
<213> ORGANISM: artificial
<220> FEATURE:
<223> OTHER INFORMATION: Lipocalin mutein (S0569.10I10M1)

<400> SEQUENCE: 14

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Gly Leu Arg Glu Asp Lys Asp Pro
        35                  40                  45
```

```
Pro Lys Met Trp Ala Thr Ile Tyr Glu Leu Lys Glu Asp Lys Ser Tyr
            50                  55                  60

Asp Val Thr Asn Val Arg Phe Ala Gly Lys Lys Val Lys Tyr Thr Ile
 65                  70                  75                  80

Gly Thr Phe Val Pro Gly Ser Gln Pro Gly Glu Phe Thr Leu Gly Gln
                    85                  90                  95

Ile Lys Ser Glu Pro Gly Asn Thr Ala Thr Leu Val Arg Val Val Ser
                100                 105                 110

Thr Asn Tyr Asn Gln His Ala Met Val Phe Phe Lys Glu Val Tyr Gln
                115                 120                 125

Asn Arg Glu Ile Phe Phe Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly

<210> SEQ ID NO 15
<211> LENGTH: 178
<212> TYPE: PRT
<213> ORGANISM: artificial
<220> FEATURE:
<223> OTHER INFORMATION: Lipocalin mutein (S0569.10D09M1)

<400> SEQUENCE: 15

Gln Asp Ser Thr Ser Asp Leu Ile Pro Ala Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Arg Ala Gly Asn Val Gly Leu Arg Glu Asp Lys Asp Pro
            35                  40                  45

Pro Lys Met Arg Ala Thr Ile Tyr Glu Leu Lys Glu Asp Lys Ser Tyr
            50                  55                  60

Asp Val Thr Gly Val Arg Phe Gly Glu Lys Lys Ile Lys Tyr Ser Ile
 65                  70                  75                  80

Gly Thr Phe Val Pro Gly Ser Gln Pro Gly Glu Phe Thr Leu Gly Gln
                    85                  90                  95

Ile Lys Ser Gln Pro Gly Asp Thr Ala Asn Leu Val Arg Val Val Ser
                100                 105                 110

Thr Asn Tyr Asn Gln His Ala Met Val Phe Phe Lys Glu Val Tyr Gln
                115                 120                 125

Asn Arg Glu Ile Phe Phe Ile Ile Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly

<210> SEQ ID NO 16
<211> LENGTH: 178
<212> TYPE: PRT
<213> ORGANISM: artificial
<220> FEATURE:
<223> OTHER INFORMATION: Lipocalin mutein (S0569.04M18M2)
```

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Gly Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asp Val Thr Gly Val Arg Phe Asp Ser Lys Lys Val Thr Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Asn Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly

<210> SEQ ID NO 17
<211> LENGTH: 10
<212> TYPE: PRT
<213> ORGANISM: artificial
<220> FEATURE:
<223> OTHER INFORMATION: SA linker and Strep-tag II

<400> SEQUENCE: 17

Ser Ala Trp Ser His Pro Gln Phe Glu Lys
1               5                   10

<210> SEQ ID NO 18
<211> LENGTH: 8
<212> TYPE: PRT
<213> ORGANISM: artificial
<220> FEATURE:
<223> OTHER INFORMATION: Strep-tag II

<400> SEQUENCE: 18

Trp Ser His Pro Gln Phe Glu Lys
1               5

<210> SEQ ID NO 19
<211> LENGTH: 534
<212> TYPE: DNA
<213> ORGANISM: artificial
<220> FEATURE:
<223> OTHER INFORMATION: Lipocalin mutein (S0569.05N06M1)

<400> SEQUENCE: 19
caggactcca cctcagacct gatcccagcc ccacctctga gcaaggtccc tctgcagcag      60
aacttccagg acaaccaatt ccaagggaaa tggtatgtcg tgggcgttgc cggaaatgct     120
ctgctgcgtg aggataagga tccgcttaaa atgagggcga ccatttacga gttgaaagaa     180

```
gataaatcat atgacgtcac cgttgtgtct ttttggagga agaaatgcca ttacaagatt      240
gggacctttg tgccggggag ccagccgggc gagtttactt taggcgatat taaaagtggg      300
ccgggccaga catcaaattt ggtccgcgtc gtgagcacca actacaacca gcatgccatg      360
gtgttcttca aggaggtgag gcagaaccgc gagtggtttg ctatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 20
<211> LENGTH: 534
<212> TYPE: DNA
<213> ORGANISM: artificial
<220> FEATURE:
<223> OTHER INFORMATION: Lipocalin mutein (S0569.05K19M1)

<400> SEQUENCE: 20

```
caggactcca cctcagacct gatcccagcc ccacctctga gcaaggtccc tctgcagcag      60
aacttccagg acaaccaatt ccaagggaaa tggtatgtcg tgggcgttgc cggaaatgtt      120
cgtctgcgtg aggataagga tccgcctaaa atgagggcga ccatttacga gttgaaagaa      180
gataaatcat atgacgtcac cggtgtgtct tttcggggga agaaatgcca ttacaagatt      240
gggacctttg tgccggggag ccagccgggc gagtttactt taggcgatat taaaagtggt      300
ccgggcgaga catcaaattt ggtccgcgtc gtgagcacca actacaacca gcatgccatg      360
gtgttcttca aggaggtgag gcagaaccgc gagtggtttt ttatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 21
<211> LENGTH: 534
<212> TYPE: DNA
<213> ORGANISM: artificial
<220> FEATURE:
<223> OTHER INFORMATION: Lipocalin mutein (S0569.05O04M1)

<400> SEQUENCE: 21

```
caggactcca cctcagacct gatcccagcc ccacctctga gcaaggtccc tctgcagcag      60
aacttccagg acaaccaatt ccaagggaaa tggtatgtcg tgggcgttgc cggaaatggt      120
atgctgcgtg aggataagga tccgcttaaa atgagggcga ccatttacga gttgaaagaa      180
gataaatcat atgacgtcac cagtgtggct tttcggaata agaaatgcca ttacaagatt      240
gggacctttg tgccggggag ccagccgggc gagtttactt taggccagat taaaagtggt      300
ccgggcgaga catcaaattt ggtccgcgtc gtgagcacca actacaacca gcatgccatg      360
gtgttcttca aggaggtgag gcagaaccgc gagtggtttt ttatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 22
<211> LENGTH: 534
<212> TYPE: DNA
<213> ORGANISM: artificial
<220> FEATURE:
<223> OTHER INFORMATION: Lipocalin mutein (S0569.02J22M1)

<400> SEQUENCE: 22

```
caggactcca cctcagacct gatcccagcc ccacctctga gcaaggtccc tctgcagcag    60
aacttccagg acaaccaatt ccaagggaaa tggtatgtcg tgggcagggc cggaaatgtg   120
gggctgcgtg aggataagga tccgcctaaa atgtgggcga ccatttacga gttgaaagaa   180
gataaatcat atgacgtcac caatgtgagg tttgctagga gaaatgctt gtactcgatt   240 gggacctttg tgccggggag ccagccgggc gagtttactt taggccagat taaaagtgag   300
ccgggcaata cagcaaattt ggtccgcgtc gtgagcacca actacaacca gcatgccatg   360
gtgttcttca aggaggtgta tcagaaccgc gagattttt ttatcatact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 23
<211> LENGTH: 534
<212> TYPE: DNA
<213> ORGANISM: artificial
<220> FEATURE:
<223> OTHER INFORMATION: Lipocalin mutein (S0569.02B06M1)

<400> SEQUENCE: 23

```
caggactcca cctcagacct gatcccagcc ccacctctga gcaaggtccc tctgcagcag    60
aacttccagg acaaccaatt ccaagggaaa tggtatgtcg tgggcagggc cggaaatgtg   120
ggtctgcgtg aggataagga tccgcctaaa atgtgggcga ccatttacga gttgaaagaa   180
gataaatcat atgacgtcac caatgtgagg tttgctagga gaaatgcac gtactcgatt   240 gggacctttg tgccggggag ccagccgggc gagtttactt taggccagat taaaagtgag   300
ccgggcggta cagcaaattt ggtccgcgtc gtgagcacca actacaacca gcatgccatg   360
gtgttcttca aggaggtgta tcagaaccgc gagattttt ttatcatact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 24
<211> LENGTH: 534
<212> TYPE: DNA
<213> ORGANISM: artificial
<220> FEATURE:
<223> OTHER INFORMATION: Lipocalin mutein (S0569.02L21M1)

<400> SEQUENCE: 24

```
caggactcca cctcagacct gatcccagcc ccacctctga gcaaggtccc tctgcagcag    60
aacttccagg acaaccaatt ccaagggaaa tggtatgtcg tgggcagggc cggaaatggg   120
gctctgcgtg aggataagga tccgcctaaa atgtgggcga ccatttacga gttgaaagaa   180
gataaatcat atgacgtcac caatgtgagg tttgctagga gaaatgcgt gtactcgatt   240 gggacctttg tgccggggag ccagccgggc gagtttactt taggcccgat taaaagtgag   300
ccgggcaata cagcatcttt ggtccgcgtc gtgagcacca actacaacca gcatgccatg   360
gtgttcttca aggaggtgta tcagaaccgc gagattttt ttatcatact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 25
<211> LENGTH: 534
<212> TYPE: DNA
<213> ORGANISM: artificial

<220> FEATURE:
<223> OTHER INFORMATION: Lipocalin mutein (S0569.02A11M1)

<400> SEQUENCE: 25

```
caggactcca cctcagacct gatcccagcc ccacctctga gcaaggtccc tctgcagcag    60
aacttccagg acaaccaatt ccaagggaaa tggtatgtcg tgggcagggc cggaaatgtt   120
gctctgcgtg aggataagga tccgcctaaa atgagggcga ccatttacga gttgaaagaa   180
gataaatcat atgacgtcac cgctgtgagg tttgctagga gaaatgcct gtactcgatt    240
gggacctttg tgccggggag ccagccgggc gagtttactt taggccggat taaaagtgag   300
ccgggctata cagcaaattt ggtccgcgtc gtgagcacca actacaacca gcatgccatg   360
gtgttcttca aggaggtgta tcagaaccgc gagattttttt ttatcatact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 26
<211> LENGTH: 534
<212> TYPE: DNA
<213> ORGANISM: artificial
<220> FEATURE:
<223> OTHER INFORMATION: Lipocalin mutein (S0569.09P24M1)

<400> SEQUENCE: 26

```
caggactcca cctcagacct gatcccagcc ccacctctga gcaaggtccc tctgcagcag    60
aacttccagg acaaccaatt ccaagggaaa tggtatgtcg tgggcagggc cggaaatgtg   120
gctctgcgtg aggataagga tccgcctaaa atgagggcga ccatttacga gttgaaagaa   180
gataaatcat atgacgtcac caatgtggtg tttgctggga gaaatgcaa gtactcgatt    240
gggacctttg tgccggggag ccagccgggc gagtttactt taggccggat taaaagtccg   300
ccgggcaata cagcaaattt ggtccgcgtc gtgagcacca actacaacca gcatgccatg   360
gtgttcttca aggaggtgta tcagaaccgc gagattttttt ttatcatact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 27
<211> LENGTH: 534
<212> TYPE: DNA
<213> ORGANISM: artificial
<220> FEATURE:
<223> OTHER INFORMATION: Lipocalin mutein (S0569.02N03M1)

<400> SEQUENCE: 27

```
caggactcca cctcagacct gatcccagcc ccacctctga gcaaggtccc tctgcagcag    60
aacttccagg acaaccaatt ccaagggaaa tggtatgtcg tgggcagggc cggaaatctg   120
ggtctgcgtg aggataagga tccgcctaaa atgtgggcga ccatttacga gttgaaagaa   180
gataaatcat atgacgtcac caatgtgagg tttgctagga gaaatgcat gtactctatt    240
ggtacctttg tgccggggag ccagccgggc gagtttactt taggccagat taaaagtgag   300
ccgggcagta cagcaaattt ggtccgcgtc gtgagcacca actacaacca gcatgccatg   360
gtgttcttca aggaggtgta tcagaaccgc gagattttttt ttatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 28
<211> LENGTH: 534
<212> TYPE: DNA
<213> ORGANISM: artificial
<220> FEATURE:
<223> OTHER INFORMATION: Lipocalin mutein (S0569.10I10M1)

<400> SEQUENCE: 28

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccaagggaaa | tggtatgtcg | tgggcagggc | cggaaatgtg | 120 |
| ggtctgcgtg | aggataagga | tccgcctaaa | atgtgggcga | ccatttacga | gttgaaagaa | 180 |
| gataaatcat | atgacgtcac | caatgtgagg | tttgctggga | agaaagttaa | gtacacgatt | 240 |
| gggacctttg | tgccggggag | ccagccgggc | gagtttactt | taggccagat | taaaagtgag | 300 |
| ccgggcaata | cagcaacttt | ggtccgcgtc | gtgagcacca | actacaacca | gcatgccatg | 360 |
| gtgttcttca | aggaggtgta | tcagaaccgc | gagattttt | ttatcacact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | aggctatcga | cggc | 534 |

<210> SEQ ID NO 29
<211> LENGTH: 534
<212> TYPE: DNA
<213> ORGANISM: artificial
<220> FEATURE:
<223> OTHER INFORMATION: Lipocalin mutein (S0569.10D09M1)

<400> SEQUENCE: 29

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccaagggaaa | tggtatgtcg | tgggcagggc | cggaaatgtg | 120 |
| ggtctgcgtg | aggataagga | tccgcctaaa | atgagggcga | ccatttacga | gttgaaagaa | 180 |
| gataaatcat | atgacgtcac | cggtgtgagg | tttggtgaga | agaaaattaa | gtactcgatt | 240 |
| ggtacctttg | tgccggggag | ccagccgggc | gagtttactt | taggccagat | taaaagtcag | 300 |
| ccgggcgata | cagcaaattt | ggtccgcgtc | gtgagcacca | actacaacca | gcatgccatg | 360 |
| gtgttcttca | aggaggtgta | tcagaaccgc | gagattttt | ttatcatact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | aggctatcga | cggc | 534 |

<210> SEQ ID NO 30
<211> LENGTH: 534
<212> TYPE: DNA
<213> ORGANISM: artificial
<220> FEATURE:
<223> OTHER INFORMATION: Lipocalin mutein (S0569.04M18M2)

<400> SEQUENCE: 30

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccaagggaaa | tggtatgtcg | tgggccgggc | cggaaatgtg | 120 |
| ggtctgcgtg | aggataagga | tccgcctaaa | atgagggcga | ccatttacga | gttgaaagaa | 180 |
| gataaatcat | atgacgtcac | cggtgtgagg | tttgattcta | agaaagtgac | gtactctatt | 240 |
| gggacctttg | tgccggggag | ccagccgggc | gagtttactt | taggccagat | taaaagtgag | 300 |

| | | |
|---|---|---|
| ccgggcaata cagcgaattt ggtccgcgtc gtgagcacca actacaacca gcatgccatg | 360 |
| gtgttcttca aggaggtgta tcagaaccgc gagattttt ttatcatact gtacgggcgc | 420 |
| acgaaagaac tgacaagcga gctgaaggaa aattttatcc gcttttccaa atctctgggc | 480 |
| ctccctgaaa accacatcgt cttccctgtc ccaatcgacc aggctatcga cggc | 534 |

UNITED STATES PATENT AND TRADEMARK OFFICE
CERTIFICATE OF CORRECTION

PATENT NO. : 10,787,491 B2  
APPLICATION NO. : 16/389115  
DATED : September 29, 2020  
INVENTOR(S) : Marlon Hinner et al.

Page 1 of 1

It is certified that error appears in the above-identified patent and that said Letters Patent is hereby corrected as shown below:

In the Claims

In Claim 1, Column 63, Line 23, replace:
"Tyr 52 Arg"
With:
--Tyr 52→Arg--

In Claim 7, Column 63, Line 57, replace:
"Tyr 52 Arg"
With:
--Tyr 52→Arg--

In Claim 7, Column 63, Line 65, replace:
"Tyr 52 Arg"
With:
--Tyr 52→Arg--

In Claim 7, Column 64, Line 14, replace:
"Tyr 52 Arg"
With:
--Tyr 52→Arg--

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*